(12) United States Patent
Imai et al.

(10) Patent No.: US 6,742,529 B2
(45) Date of Patent: Jun. 1, 2004

(54) RESIN RECYCLING SYSTEM

(75) Inventors: Takateru Imai, Tokyo (JP); Kenichi Urabe, Tokyo (JP); Kouji Ishikawa, Tokyo (JP)

(73) Assignee: Techno Polymer Co., Ltd., Tokyo (JP)

( * ) Notice: Subject to any disclaimer, the term of this patent is extended or adjusted under 35 U.S.C. 154(b) by 137 days.

(21) Appl. No.: 09/939,388

(22) Filed: Aug. 24, 2001

(65) Prior Publication Data

US 2002/0062844 A1 May 30, 2002

(30) Foreign Application Priority Data

Aug. 25, 2000 (JP) .......................................... 2000-256202
Feb. 23, 2001 (JP) .......................................... 2001-047750

(51) Int. Cl.[7] ................................................. B08B 3/00
(52) U.S. Cl. ................................ 134/63; 134/61; 134/62; 134/184; 134/186; 134/190; 134/200; 134/25.1; 134/6; 241/38; 241/68; 241/98; 241/DIG. 38
(58) Field of Search ............................... 521/405, 465, 521/47; 524/502; 134/61, 65, 184, 186, 190, 200, 25.1, 6, 62, 63; 241/38, 68, 98, DIG. 38

(56) References Cited

U.S. PATENT DOCUMENTS

| | | |
|---|---|---|
| 1,773,476 A | 8/1930 | Crusher |
| 4,566,641 A | 1/1986 | Okamoto et al. |
| 5,282,713 A | 2/1994 | Lande |
| 5,365,075 A * | 11/1994 | Peterson ................. 250/559.02 |
| 5,443,652 A | 8/1995 | Scarola et al. |
| 5,489,778 A | 2/1996 | Burmester et al. |
| 5,567,106 A | 10/1996 | Gassner |
| 5,964,563 A | 10/1999 | Bielagus et al. |
| 6,025,910 A | 2/2000 | Lucas |
| 6,372,807 B1 * | 4/2002 | Szekely ...................... 521/40.5 |

FOREIGN PATENT DOCUMENTS

| | | |
|---|---|---|
| DE | 092 17 165 | 2/1993 |
| DE | 043 05 006 | 9/1993 |
| DE | 043 02 283 | 7/1994 |
| DE | 043 38 561 | 5/1995 |
| DE | 195 45 240 | 5/1997 |
| DE | 19800521 | 7/1999 |
| DE | 199 49 656 | 4/2001 |
| DE | 10006740 | 8/2001 |
| EP | 0 129 518 | 12/1984 |
| EP | 0 706 043 | 4/1996 |
| EP | 1023945 | 8/2000 |
| EP | 1 153 720 | 11/2001 |
| GB | 2330 409 | 4/1999 |
| JP | 10038807 | 2/1998 |
| JP | 2001030251 | 2/2001 |
| NL | 8 303 265 | 4/1985 |
| WO | WO 96/27045 | 9/1996 |
| WO | WO 99/34927 * | 1/1999 |
| WO | WO 200045994 A1 * | 1/2000 |

* cited by examiner

Primary Examiner—M. Kornakov
(74) Attorney, Agent, or Firm—Fitch, Even, Tabin & Flannery

(57) ABSTRACT

A system for recycling reusable resin mold products recovered from discarded apparatuses is disclosed. This recycling system includes a crushing system for crushing resin mold products one kind by one kind into crushed resinous pieces and packing the same in a bag, a classification system for irradiating a light beam to the resin in the bag and classifying the bags into respective kinds of resins based on a reflected beam therefrom, a cleaning system for separately cleaning the respective kind of crushed resinous pieces taken out of the bag to remove foreign matters adhered onto the surfaces of the crushed resinous pieces therefrom, and a recovery system for recovering the cleaned crushed resinous pieces.

4 Claims, 21 Drawing Sheets

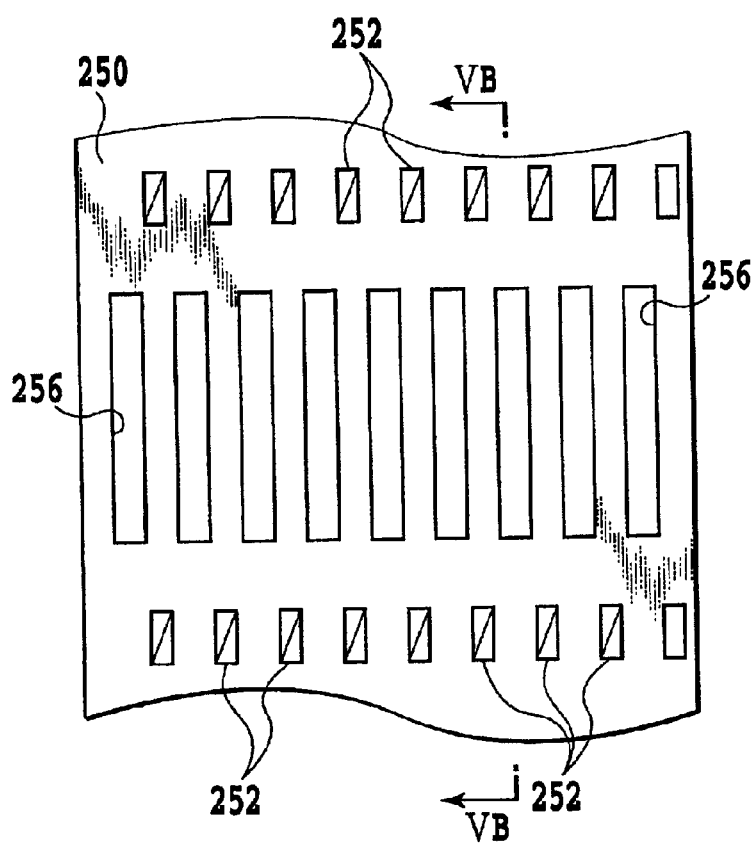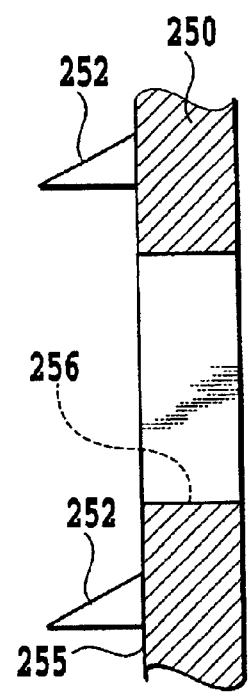
FIG.5A  FIG.5B

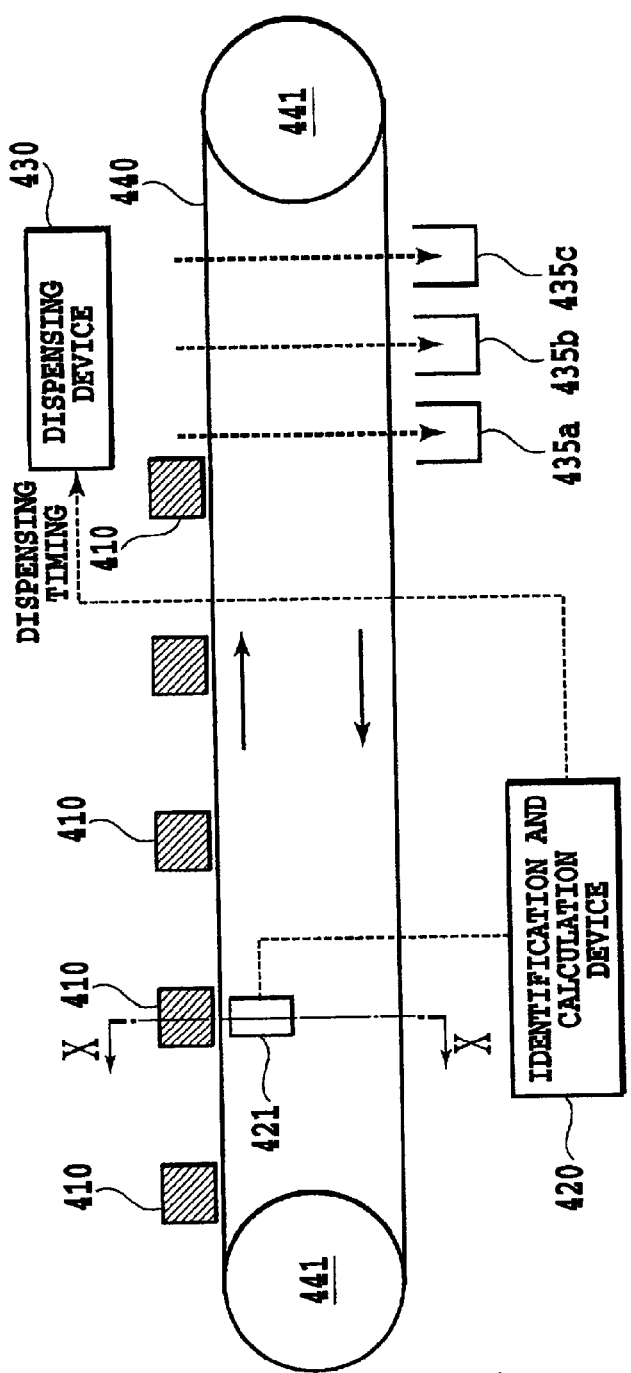
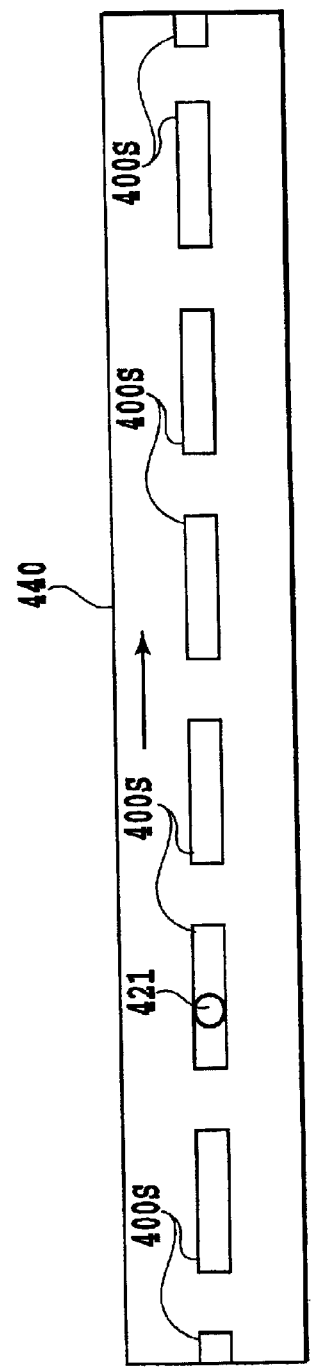
FIG.9A
FIG.9B

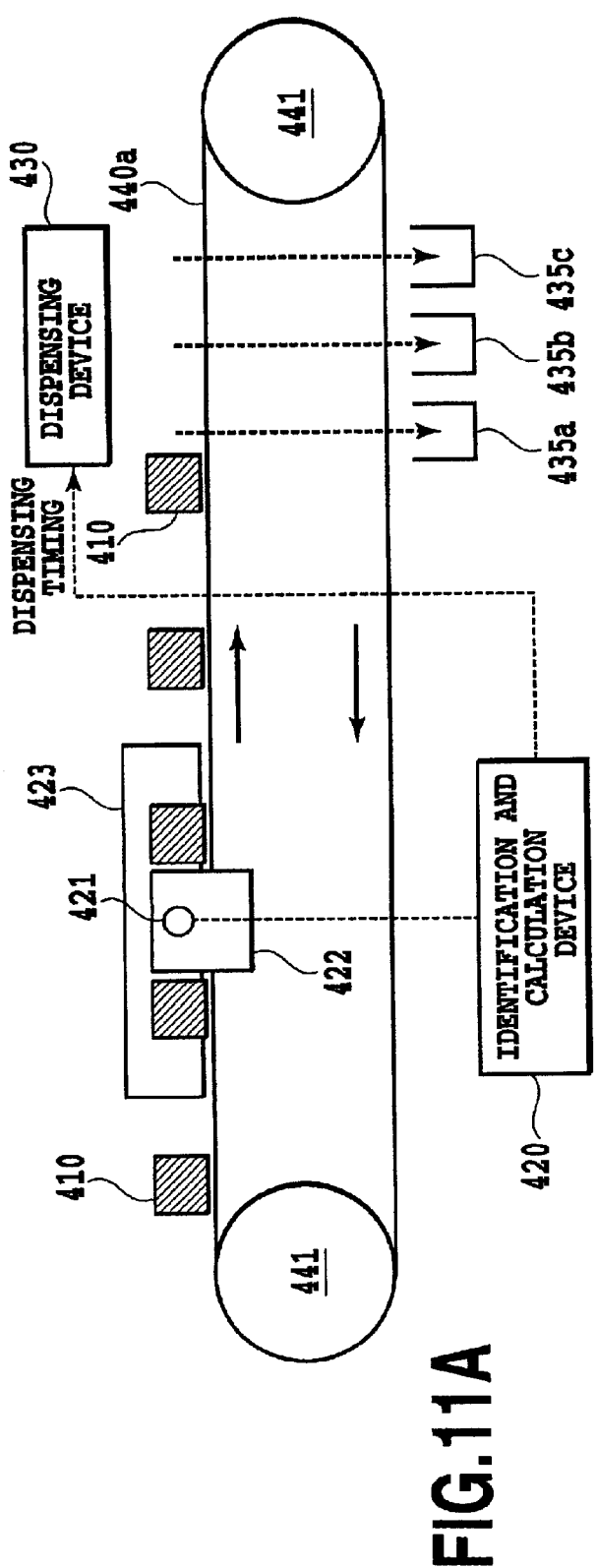
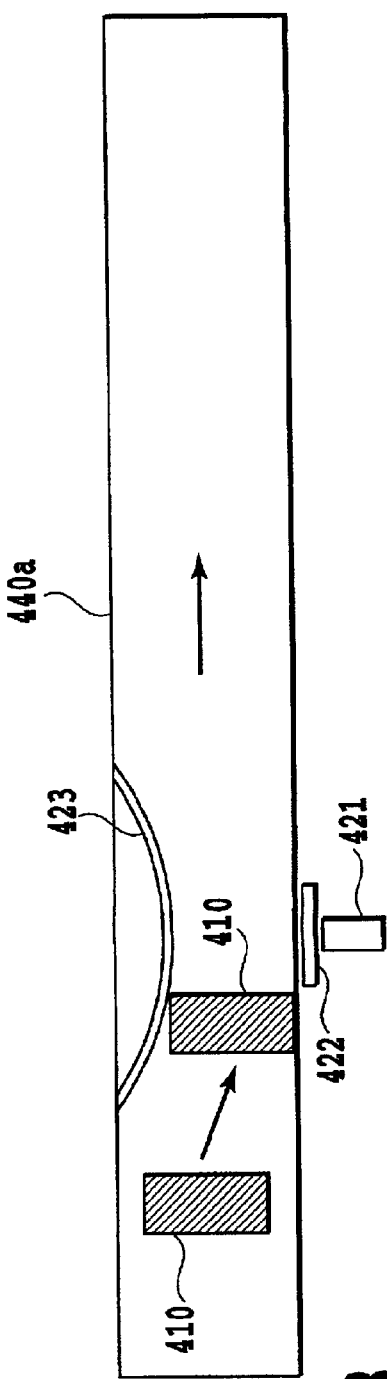
FIG.11A
FIG.11B

|  | EXAMPLE A | COMPARATIVE EXAMPLE A |
|---|---|---|
| TOTAL APPARENT VOLUME OF RESIN PARTS PRIOR TO BEING CRUSHED | 130L | 130L |
| TOTAL WEIGHT OF RESIN PARTS PRIOR TO BEING CRUSHED | 11.3kg | 11.3kg |
| BULKING DENSITY OF RESIN PARTS PRIOR TO BEING CRUSHED | 0.09 | 0.09 |
| BULKING DENSITY AFTER BEING CRUSHED | 0.48 | 0.62 |
| AVERAGE VALUE OF EQUIVALENT DIAMETERS OF CRUSHED RESINOUS PIECES | 35mm | 7mm |
| TOTAL WEIGHT OF CRUSHED RESINOUS PIECES | 11.2kg | 2.3kg |
| APPARENT VOLUME OF CRUSHED RESINOUS PIECES | 23.3L | 3.7L |
| ESTIMATION | ALL THE PARTS WERE CRUSHED TO REDUCE THEIR VOLUME | ONLY FIVE PARTS (2.3 KG) WERE CRUSHED TO FAIL THE REDUCTION OF VOLUME |

FIG.17

| ESTIMATION | EXAMPLE B | COMPARATIVE EXAMPLE B |
|---|---|---|
| TOTAL VOLUME OF RESIN PARTS PRIOR TO BEING CRUSHED (cm$^3$) | 4500 | 4500 |
| TOTAL VOLUME OF RESIN PARTS AFTER BEING CRUSHED (cm$^3$) | 1115 | 1060 |
| RATIO OF VOLUMES BETWEEN BEFORE AND AFTER BEING CRUSHED #1 | 4.0 | 4.2 |
| NUMBER OF IDENTIFIED SAMPLES (PIECES) | 3 | ABOUT 2700#2 |
| TIME REQUIRED FOR THE IDENTIFICATION (min) | 0.15 | ABOUT 135#3 |
| IDENTIFIED RESULT | ○ | × |

1: (VOLUME OF RESIN PARTS PRIOR TO BEING CRUSHED) / (TOTAL VOLUME OF RESIN PARTS AFTER BEING CRUSHED)
2: IT WAS ESTIMATED BY (WEIGHT OF RESIN PARTS PRIOR TO BEING CRUSHED) / (STANDARD WEIGHT OF ONE CRUSHED RESINOUS PIECE)
3: IT WAS ESTIMATED BY (TOTAL WEIGHT OF CRUSHED RESINOUS PIECES) / (WEIGHT OF CRUSHED RESINOUS PIECES IDENTIFIABLE PER ONE MINUTE)

FIG.18

| | EXAMPLE C | COMPARATIVE EXAMPLE C | COMPARATIVE EXAMPLE D | EXAMPLE D | COMPARATIVE EXAMPLE E | EXAMPLE E | COMPARATIVE EXAMPLE F |
|---|---|---|---|---|---|---|---|
| NUMBER OF FOREIGN MATTERS | FOREIGN MATTERS HAVING MAXIMUM LENGTH IN A RANGE FROM 0.05 TO 0.25 mm | 3 | | NUMEROUS | 4 | | 4 | NUMEROUS |
| | FOREIGN MATTERS HAVING MAXIMUM LENGTH IN A RANGE FROM 0.25 TO 0.5 mm | 0 | — | NUMEROUS | 0 | IMPOSSIBLE TO MEASURE BECAUSE OF COATED FILM RESIDUE | 0 | 50 MORE |
| | FOREIGN MATTERS HAVING MAXIMUM LENGTH IN A RANGE FROM 0.5 mm OR MORE | 0 | | 50 MORE | 0 | | 0 | 30 |
| NOTE | | — | INOPERATIVE | LABEL PIECE LEFT | — | MUCH COATED FILM RESIDUE | — | — |
| ESTIMATION | | GOOD | NO GOOD | NO GOOD | GOOD | NO GOOD | GOOD | NO GOOD |

FIG.19

RESIN RECYCLING SYSTEM

This application is based on Patent Application Nos. 2000-256202 filed Aug. 25, 2000 in Japan and 2001-047750 filed Feb. 23, 2001 the content of which is incorporated hereinto by reference.

BACKGROUND OF THE INVENTION

1. Field of the Invention

The present invention relates to a system for recycling resinous materials from resin mold products recovered from discarded apparatuses (such as home electric appliances, electronic devices or cars), more particularly to a crushing system for crushing polymer parts obtained by disassembling the recovered products to reduce the volume thereof; a classifying system for classifying the resinous materials into their kinds, preferably into kinds of fire retardants added thereto; and a cleaning system for removing foreign matters such as coated films, labels or seals applied to the products or other contamination thereof.

2. Description of the Related Art

Plastics light in weight and excellent in mechanical strength have often been used for home electric appliances, OA apparatuses, communication apparatuses or others as internal parts or external casings thereof. From a point of view of the environmental protection, the conversion from a mass-production/mass-scrap economy in the past to a circulation type economy is required. In such a recent trend, a full-scale recycle of resinous products has been urgently demanded; for example, the recycling of home electric appliances has been obligated by law. However, regarding the material recycle in which the resin mold products are recovered and reused as resinous materials, it is done solely in a case wherein it is possible to specify to some extent what kind of resin is used, because there is a problem peculiar to the resin in that if different kinds of resins are mixed together, functions inherent to the resin are significantly damaged. Accordingly, a resin recycling system is desired, which is capable of correctly classifying various kinds of resinous products used in the discarded appliances or apparatuses and regenerating the same as fresh resinous materials for the home electric appliances, OA apparatuses or communication apparatuses.

To proceed a high-quality recycling, it is necessary to correctly identify and classify materials of resin mold products containing various kinds of additives including fire retardant. Regarding the identification of materials of the resin mold products, a high-performance resin identification device has recently been developed, and is becoming reality. This device, however, necessitates a considerable care on the operation, maintenance and inspection thereof as well as it is expensive in cost. The most effective method for identifying materials of the resin mold products solely from a point of view of the material identification is to provide such a resin identification device in each of the disassembly factories. This method is, however, problematic from the economical view point or a view point of stable operation of the system.

To operate the above-mentioned resin identification device under the stably controlled condition, it is desirable to provide the disassembly factory for recovering the resin mold products at a position different from that of the resin identification device. In such a case, it is necessary to convey the resin mold products from the disassembly factory to the position at which the resin identification device is provided.

However, the resin mold products obtained from the discarded apparatuses have various shapes and sizes distributed from a small one to an extremely large one. Therefore, if they are packed into a box or a bag while maintaining their shapes, the physical transportation cost becomes wasteful since a bulk specific weight is very small to reduce a weight relative to a volume thereof. Accordingly, it is desired to crush the resin mold products into pieces having an economically preferable size (a size capable of achieving a proper transportation efficiency). As a crusher used for this purpose, it is possible to use a commercially available crusher such as a hammer mill, a cutter mill, a two-axis crusher and the like which is capable of crushing the resin mold products into pieces having about 50 mm or less in size.

However, the resin mold products recovered from disassembling appliances have various sizes as set forth above. In order to load all of the resin mold products and crush them into pieces having about 50 mm or less in size, it becomes necessary to provide a very big crusher having a loading opening. Since these equipment is costly, there is a problem that it is economically impossible to install such expensive equipment at each of small factories.

Further, if the resin mold products are crushed altogether by such means, however, many of the resin mold products formed of different kinds of resins are crushed in a mixed state, and, as a result, it is necessary to identify crushed pieces in which many kinds of resins exist using an identification apparatus. Although such identification is possible in principle, industrialization thereof is difficult in practice because it is necessary to respectively identify kinds of resins of a large number of crushed pieces and classify the same into the respective materials after the identification.

In addition, to economically realize the material recycling of high-quality resinous materials, it is necessary to classify kinds of resins containing various additives such as fire retardant at a high accuracy and a high speed. As a method for classifying the kinds of resins, a technique using, for example, a near infrared ray absorption has been known and various devices are marketed. However, this method hardly identifies kinds of resins with many identification errors and is unsuitable for the high accuracy and high speed identification. Another method utilizing intermediate infrared absorption has been also known. Although this method is capable of identifying not only kinds of resins but also those of additives such as fire-retardant at a high accuracy, there is a problem in that a long time is required for the identification and therefore unsuitable for a high speed processing.

On the other hand, the recovered resinous products may be coated with films, applied with labels or the like or carry various contaminants, which are liable to enter the resin during the treatment of the resinous products to result in a problem to significantly deteriorate the characteristic of the resin to be reused.

Although various trials have been attempted for removing foreign matters carried on the surface of the resinous product, for example, by a mechanical method and the separation or removal with a solvent, there is a problem in either cases. For instance, if the removal of the coated film or the label is intended by using a crusher such as a ball mill, the resin is softened due to heat generated by the friction during the crushing operation, which disturbs the resin removal or causes the re-adhesion of the foreign matters once removed. Also, there is another method wherein the foreign matters are dissolved with a solvent and then separated and removed from the resin. This method, however, has a serious problems in that the used solvent must be regenerated or discarded, and also has other problems in that an apparatus used therefor is complicated in structure and unfavorable from the economical point of view.

There is a still further method for removing the coated film or labels, called as a dry blast treatment, wherein an abrasive material such as sands or metallic particles is used for scraping off the foreign matters from the surface of the resinous product. According to this method, however, particles of the abrasive material may stick into the surface of the resinous product and remain as they are as new foreign matters. Also, the resin may be softened by heat generated due to the friction of the abrasive material and cause the re-adhesion of the foreign matters once removed.

SUMMARY OF THE INVENTION

The present invention has been done to solve the above-mentioned problems, and an object of the present invention is to provide a resin recycling system for crushing resin mold products collected from discarded apparatuses into crushed resinous pieces to reduce an apparent volume thereof, without identifying that the resin mold product belongs to what kind of resin but with taking care that a plurality of kinds of resins are not mixed with each other; identifying a kind of the crushed resinous pieces to classify the same to that kind for easily determining a field in which the same is reused; and removing foreign matters from the surface of the classified crushed resinous piece to be reusable as resinous material.

Another object of the present invention is to provide a crushing system for roughly crushing polymer parts (including a large-sized ones) taken out from the collected and disassembled apparatuses to reduce an apparent volume thereof.

A further object of the present invention is to provide an identification system for effectively identifying a kind of crushed resinous pieces obtained by crushing resin mold products collected from discarded electric or electronic equipment without identifying that the resin mold product belongs to what kind of resin but with taking care that a plurality of kinds of resins are not mixed with each other.

Further, the present invention is to solve the above-mentioned problems of the prior art by providing a cleaning system for thermoplastic resin products wherein, when the resin products are collected and cleaned to be reusable resinous material, foreign matters such as coated films or labels adhered on the surface of the resin products are sufficiently removed therefrom so that the resinous material is usable in the same field as before.

To achieve the above objects, according to one aspect of the present invention, a resin recycling system is provided, which comprises crushing means for individually crushing resin mold products into crushed resinous pieces in which 70% or more of the crushed resinous pieces have an equivalent diameter in a range from 1 to 50 mm, packing means for packing the crushed resinous pieces of the respective mold product into a bag having a transparent portion, classification means for irradiating a light beam to the crushed resinous pieces in the bag through the transparent portion, identifying a kind of the crushed resinous pieces based on a reflected beam therefrom, and classifying the bags into respective kinds of resins, and cleaning means for taking the crushed resinous pieces out from the bag and cleaning the crushed resinous pieces of the respective kind to remove foreign matters adhered on the surface thereof.

In the above description, the term, "equivalent diameter" is a diameter of a circle having the same area as that of a projected area of an object.

Here, the equivalent diameter of the crushed resinous piece is preferably in a range from 3 to 40 mm, more preferably from 5 to 30 mm. A ratio of the crushed resinous pieces having the equivalent diameter within these ranges is preferably 80% or more, more preferably 90% or more.

If the equivalent diameter of the crushed resinous piece is smaller than 1 mm, there is an inconvenience in that foreign matters could not be removed during cleaning by the cleaning means, because the crushed resinous piece is pulverized. For example, when the cleaning is carried out by the abrasion, the abrasion becomes impossible. Also, the small resinous pieces are liable to stick to the interior of the crusher or the bag due to static electricity.

On the other hand, if the equivalent diameter of the crushed resinous piece exceeds 50 mm, the crushed resinous pieces may be still three-dimensional to obstruct the sufficient volume reduction.

The crushing may be carried out at one step. However, if the mold product is too large in size to be introduced into an ordinary crusher, the crushing may be carried out at two steps wherein the mold product is roughly crushed by a rough crusher and then introduced into the ordinary crusher.

Since one resin mold product is formed of one kind of resin, it is possible to effectively reduce the apparent volume of the resin mold product while preventing the finely crushed resinous pieces from mixing with other kinds by crushing the resin mold product separately one kind by one kind and immediately packing into a bag. By crushing the resin mold product one by one which is recovered from the discarded apparatus in the manual disassembly factory and packing the crushed resinous pieces in a bag, the conveying efficiency is enhanced.

Since the crushed resinous pieces in the bag is of the same kind of resin, it is possible to carry out the economical classification by classifying the bags.

In this regard, to further enhance the working efficiency, when it is apparent in advance that the mold products are formed of the same kind of resin, they are crushed together and packed in one bag. For example, if there are plurality of mold members of the same shape and function (such as paper feeding trays of different sizes of a copying machine) and it is confirmed that they are formed of the same kind of resin, they may be crushed together and packed in one bag. This method is favorable for facilitating the working efficiency when there are a number of small resinous members of a similar shape and the same kind of resin in one discarded apparatus.

The transparent portion of the bag is necessary for the purpose of preventing the light beam irradiated to the crushed resinous particles or reflected therefrom from being adversely effected by the passage thereof through the bag. Accordingly, if the adverse effect on the detection due to the passage of light beam through the bag is negligible, the transparent portion is not necessarily completely transparent. In short, it is sufficient that the bag is provided with a light-passing area (transparent portion) which does not adversely effect the detection, and in this text, such a light-passing area is referred to as a transparent portion. The transparent portion may extend throughout the bag. Such a bag may be formed, for example, of polyethylene. In this regard, a thickness of the transparent portion is generally 100 $\mu$m or less. Other materials may be used for this purpose, such as resinous film, resinous net or metallic net.

A method for identifying a kind of resin includes, for example, one based on a Raman spectrum analysis, wherein a Raman spectrum obtained from the reflected light beam from the resin to be inspected (i.e., the crushed resinous pieces in the bag) is sequentially compared with Raman spectra obtained from reflected light beams from various known resins prepared in advance to find whether or not there is the coincidence between both the spectra. The method based on the Raman spectrum analysis is favorable because it is less adversely effected from color tone or surface contamination of the crushed resinous piece. One method for identifying kind of resin based on the Raman spectrum analysis is disclosed, for example, in paragraphs from 0011 to 0018 of Japanese Patent Application Laid-open No. 10-38807. Alternatively, an infrared or near infrared spectrum analysis may be used for this purpose.

One method for classifying the bags into kinds of resins includes the steps of storing an identified kind of crushed resinous pieces and an expected arrival time at which the bag of the crushed resinous pieces would reach a predetermined classification position on a conveying path, in correspondence to each other, and recovering the bag reaching the classification position at the expected arrival time from the conveying path.

The predetermined classification position may be different in accordance with kinds of resins. In such a case, the classified recovery is carried out wherein, for example, the bag in which resin A is packed is recovered from the conveying path at the classification position for the resin A, and the bag in which resin B is packed is recovered from the conveying path at the classification position for the resin B.

The predetermined position may be a specified one irrespective of kinds of resins. In such a case, the classified recovery is carried out in such a manner that the bag of resin A (the resin A is packed) reaching the classification position is guided from the conveying path to a collecting container or the like for the resin A, and similarly, the bag of resin B reaching the classification position is guided from the conveying path to a collecting container or the like for the resin B.

The expected arrival time is obtained by an identification time, a distance between an identification position and the classification position, and a conveying speed. While the expected arrival time may be calculated from these data every time, it may be determined as a time a predetermined period after an identification time, since the above distance and the conveying speed are constant.

The cleaning means removes foreign matters such as plated layers, coatings, labels or contaminants adhered to the surface of the crushed resinous piece therefrom.

The cleaning means may be a device having a cleaning vessel and an agitator member provided in the cleaning vessel wherein at least part of the inner wall of the cleaning vessel and/or a surface of the agitator member has an abrasive surface (roughened surface) for removing (scraping or scrubbing off) the foreign matters on the surface of the crushed resinous piece. Water or an aqueous rinsing liquid may be supplied into the vessel to enhance the removal of foreign matters.

The abrasive surface (roughened surface) may be of any structure, provided it could sufficiently clean the surface of the crushed resinous piece. The abrasive surface preferably has the irregularity having a depth in a range from 40 to 2000 $\mu$m. By the contact of crushed resinous pieces with this roughened surface having such irregularity, foreign matters such as coated film or label adhered onto the surface of the crushed resinous piece are sufficiently scrubbed or scraped off and removed. If the depth of the irregularity is less than 40 $\mu$m, the foreign matters are not sufficiently removable. Contrarily, if exceeding 2000 $\mu$m, the surface of the crushed resinous piece is excessively scraped off to lower the resin recovery percentage. The depth of the irregularity is preferably in a range from 50 to 1000 $\mu$m, more preferably from 60 to 500 $\mu$m. If the depth is within such a range, the foreign matters are not excessively scraped off but sufficiently removable.

In the device for continuously cleaning the crushed resinous pieces, the crushed resinous pieces are continuously supplied from one end of the cleaning vessel, conveyed in one direction within the cleaning vessel, for example, by a screw or others and continuously collected from the other end. If water or aqueous liquid is used in such a device, the feeding of water or aqueous liquid is carried out in a similar manner that the water or the aqueous liquid is also continuously fed from the one end and/or intermediate portions of the cleaning vessel, flows in the same direction in the cleaning vessel and is continuously drained from the other end.

When water or aqueous liquid is used during the cleaning operation, it functions as a lubricant between the crushed resinous pieces and the irregularity to prevent the surface of the crushed resinous piece from being excessively scraped off as well as to suppress the temperature rise of the crushed resinous piece due to the cooling operation of water whereby the softening thereof is inhibited. Also, the foreign matters such as coated film or label once removed are quickly discharged out of the cleaning device and do not adhere again to the crushed resinous pieces.

The resin recycling system may have a recovery means for separating foreign matters from a mixture of the crushed resinous pieces cleaned by the cleaning means and the foreign matters and recover the crushed resinous pieces. The crushed resinous pieces and the foreign matters may be separated from each other, for example, by wind. Also, magnet force may be used for removing metallic material. When water or aqueous liquid is used for the cleaning operation, it is possible to remove foreign matters together with water or the like. In this regard, it may be so adapted that, after removing foreign matters from water or aqueous liquid through a filter or others, the water or aqueous liquid is reused.

The resin mold products which can be recycled after being crushed, classified and cleaned according to the present invention include, for example, those used as housings or parts of various apparatuses used in an OA and home electric appliance field, an electric and electronic field, a sanitary field, an automobile field or a sundries field. For example, various resinous housings, trays or internal resinous parts used in copying machines, printers, personal computers, TV sets, various monitors or mobile telephones.

The resinous material recycled according to the present invention includes, for example, various styrene type resins such as acrylonitrile-butadiene-styrene resin, polystyrene resin or acrylonitrile-styrene resin; polycarbonate resin; olefin type resin such as polyethylene or polypropylene; polyamide type resin such as PA 6, PA66, PA46 or PA12; polyester type resin such as polybutylene terephthalate, polyethylene terephthalate or polyacrylate; polyphenylene ether resin; polyacetal; polyvinylchloride resin; polysulfon; PPS; polyether sulfon; ethylene-vinylacetate copolymer; ethylene-ethylacrylate copolymer; EVOH; polyamide type elastomer; polyester type elastomer; and alloys in which two or more of them are mixed. These are all identifiable by the classification means of the inventive system.

The classification means of the inventive system can identify additives contained in the crushed resinous pieces, such as various fire-retardants including halogen type and phosphor type; various fire-retardant assistants such as antimony trioxide, antimony tetroxide, antimony pentoxide, chlorinated polyethylene or tetrafluoroethylene polymer; inorganic filler such as glass fiber, carbon fiber, metallic fiber or talc; anti-fungus agent, mildewcide, plasticizer, antistatic or silicone oil. These additives are identifiable if a considerable amount of them is contained in the crushed resinous piece (resin mold product), for example, 1 part by weight or more, preferably 2 parts or more in 100 parts by weight of the resin mold product.

To achieve the above objects, one aspect of the crushing system according to the present invention comprises an endless conveyor for conveying polymer mold products, and an opposed member having an opposed surface confronting at least one end of the endless conveyor on the conveying-directional side and disposed so that a distance between the opposed surface and a conveying surface of the endless conveyor becomes smaller in the conveying direction, wherein crushing edges or crushing pins are provided on at least one of the conveying surface of the endless conveyor and the opposed surface of the opposed member, to direct toward the other, whereby the polymer mold products transported by the endless conveyor are pushed into a gap between the conveyor and the opposed member and crushed with the crushing edges or pins.

The crushing edge or pin is a member having a function for crushing the polymer mold product conveyed by the endless conveyor and pushed into a gap between the same and the opposed member. That is, even though shapes thereof are different from those generally thought from the feeling of words "edge or pin", any member may be the crushing edge or pin according to the present invention, if it is provided on at least one of the conveying surface of the endless conveyor and the opposed surface of the opposed member to direct toward the other, and has the above-mentioned crushing function. The crushing edge or pin preferably has a sharp portion to be in contact with the polymer mold product because a larger crushing performance is exhibited thereby.

Preferably, the crushing edges or pins are provided on the conveying surface of the endless belt, and recesses or holes are provided on the opposed surface of the opposed member for allowing tip ends of the crushing edges or pins provided on the endless conveyor to pass through the same.

The opposed member may be a second endless conveyor.

To achieve the above-mentioned objects, one aspect of the identification system of the present invention is an identification device for irradiating a light beam to a polymer products conveyed by conveyor means, detect the reflected beam or the dispersed beam from the polymer product by a sensor element, and identify a kind of the polymer product based on the detected result, wherein the sensor element is disposed at a predetermined position in the vicinity of a conveying path of the polymer product, and a distance determination mechanism is disposed in the conveying means or in the vicinity thereof, for opposing the polymer product passing by the sensor element to the sensor element at a distance between the both.

Selectable polymers include, for example, rubber-like polymer, thermoplastic elastomer and resin. Of them, resin is more preferable. Additives in the resinous material and the selectable polymeric material are the same as described above.

The conveyor means may be an endless conveyor and the sensor element may be disposed at a predetermined position beneath the conveying path constituted by the endless conveyor, and the distance determination mechanism may be a light window provided at each of portions of the endless conveyor passing over the predetermined position.

According to this arrangement, the light beam is irradiated from beneath to the polymer conveyed on the endless conveyor through the light window, and the reflected or disperse light beam is received by the sensor element through the light window. The light window may be a mere slit but not be limited thereto. It may be formed of any light-permeable material unless it disturbs the detection of Raman disperse rays.

Alternatively, the conveyor means may be an endless conveyor and the sensor element may be disposed at a predetermined position on a side of the conveying path constituted by the endless conveyor, and the distance determination mechanism comprises a stopper member having a light window and disposed in front of the sensor element in the vicinity thereof and a guide for guiding the polymer product carried on the endless conveyor so that the polymer product is pushed against the light window of the stopper member to be able to pass by a front of the sensor element.

The stopper member has a function for limiting the displacement (deviating from the conveying direction) of the polymer pushed toward the stopper member by the guide while being conveyed on the endless conveyor at the position of the stopper member. The stopper member is provided with the light window, behind which is located the sensor element.

According to this arrangement, the polymer conveyed on the endless conveyor is guided by the guide to be brought into contact with the light window of the stopper member and irradiated with a light beam through the light window. The reflected or dispersed beam thereof is received by the sensor element through the light window. The light window may be a mere slit or be formed of any light-permeable material such as transparent glass plate not disturbing the detection of Raman disperse rays.

To achieve the above objects, one aspect of a method for cleaning thermoplastic resinous products comprises the steps of crushing the collected thermoplastic resinous products into crushed pieces, supplying the crushed pieces together with water into a cleaning device having a vessel and a rotary body disposed in a rotatable manner within the vessel, wherein at least part of the inner surface of the vessel and/or a surface of the rotary body to be in contact with the crushed resinous pieces is roughened, and rotating the rotary body to clean the crushed pieces.

According to this cleaning method, at least part of the inner surface of the vessel and/or a surface of the rotary body is roughened. The roughening may be carried out in any manners, provided the resin product could be sufficiently cleaned. Preferably, the surface irregularity has a depth in a range from 40 to 2000 $\mu$m. When the roughened surface is brought into contact with the crushed resinous pieces, foreign matters such as coated film or label adhered on the surface of the crushed resinous piece are sufficiently scrubbed or scraped off and removed. If the depth of the irregularity is less than 40 $\mu$m, the foreign matters are not sufficiently removable, while if exceeding 2000 $\mu$m, the surface of the crushed resinous piece is excessively scraped off together with resin to lower the recovery percentage of resin. The depth of the irregularity is preferably in a range from 50 to 1000 $\mu$m, more preferably from 60 to 500 $\mu$m. If the depth is within this range, the foreign matters are sufficiently removed without excessively scraping resin off from the crushed piece.

The roughened surface in the interior of the vessel is preferably 1% or more, preferably 5% or more, more preferably 10% or more of a total area of the inner surface of the vessel and the surface of the rotary body to be in contact with the crushed resinous pieces. Degrees of the surface-roughening by the irregularity may be approximately equal or unequal both in the inner surface of the vessel and in the surface of the rotary body. The degree of the irregularity may be equal or unequal throughout the roughened inner surface of the vessel and/or the roughened surface of the rotary body.

According to this cleaning method, water is continuously supplied during the cleaning operation and acts as a lubricant between the surface of the crushed resinous piece and the roughened surface having the irregularity to prevent the surface of the crushed resinous piece from excessively being scraped off. Also, by the cooling action of water, the temperature rise in the crushed resinous piece can be prevented. Foreign matters such as coated film or label which have been once removed are quickly discharged out of the cleaning device not to adhere again to the crushed resinous pieces. Further, water is preferably continuously supplied and drained so that a water level in the cleaning device is maintained constant, while taking care to maintain a ratio in weight of the crushed pieces to the water constant, because the respective crushed resinous pieces continuously supplied can be evenly cleaned.

The cleaning is preferably carried out so that the ratio in weight of the crushed pieces to the water in the cleaning device is controlled to be 1:0.3 to 2 and water is continuously supplied and drained to maintain the interior temperature of the cleaning device at 70° C. or lower. If the ratio of water is less than 0.3, the interior of the cleaning device is not sufficiently cooled, whereby the temperature rises above 70° C. to soften and melt the crushed resinous pieces, which may disturb the cleaning operation. On the other hand, if the ratio of water exceeds 2, chances of contact of the crushed resinous pieces with the inner surface of the vessel and the surface of the rotary body, particularly those roughened to have the irregularity, becomes fewer. Even if the contact occurs, the crushed resinous piece does not be sufficiently pressed onto the surface, whereby the foreign matters such as coated film or label may not be completely and effectively removed.

Further, the rotary body has a screw blade for conveying the crushed resinous pieces and cleaning plates or pins for cleaning the crushed resinous pieces around a rotary shaft, and preferably rotates so that a linear speed of a tip end of the cleaning plate or pin is in a range from 0.5 to 20 m/sec. If the linear speed is 0.5 m/sec or less, the cleaning becomes insufficient, while if exceeding 20 m/sec, the interior temperature of the device rises, whereby it is difficult to maintain the temperature at 70° C. or lower.

According to the above-mentioned method, it is possible to clean the crushed pieces of all thermoplastic resin products molded to have predetermined shapes by various molding methods such as compression molding, ejection molding or blow molding. These resin mold products may be molded either using a mold or using no mold but a mold die or others. Examples of the resin mold product include not only housings of home electric appliances such as TV sets or electric refrigerators or housings of OA equipment such as personal computers or printers but also parts of these apparatuses and/or broken ones thereof.

Although there is no limitation in kinds and shapes of the resin products, preferably, products of different kinds of resins are not mixed together. This is because, if different kinds of resins are mixed together, in general, characteristics inherent to the respective resin are largely deteriorated. Therefore, the resin products are preferably classified to the respective kinds and separately cleaned in advance. Also, the resin products may preferably be classified to have the same or similar color tones, such that products which color tones are largely different, for example, one being pale and light gray and the other being deep and dark gray, are not mixed together. If the products having largely different color tones are not mixed together, color tone of resin to be reused is easily adjustable.

Also, there is no limitation in size of the resin products, provided they can be crushed to pieces of a suitable size.

The resin products may be coated or plated. The coated film may be of any material usually used for coating resin. The plated layer may be of any metal usually used for plating resin.

The resin product is cleaned after being crushed into resinous pieces through a crushing operation in advance. The crushing operation may be carried out by a crusher usually used for crushing resin and capable of crushing the resin product into pieces of a size suitable for the cleaning, such as a hammer mill or a cutter mill. The crushing operation is preferably carried out under the forced cooling such as air cooling so that the resin product does not melt due to the heat generation.

The maximum length of the crushed resinous piece is preferably in a range from 1 to 30 mm, more preferably from 2 to 20 mm, most preferably from 3 to 10 mm. If the maximum length is less than 1 mm, micro-particles increases to dissipate the crushed resinous pieces in a pre-treatment process. On the other hand, if exceeding 30 mm, the cleaning becomes insufficient all over the surface of the crushed piece. There is no limitation in shape of the crushed resinous piece provided no problem occurs in the handling thereof. However, an excessively elongated one is unfavorable, and one having generally equal dimensions in all directions in a plan view is preferable, such as circular or square. Crushed resinous pieces of such a shape can be effectively cleaned even if an amount thereof is large. In this regard, if necessary, small crushed resinous pieces having the maximum length of approximately 1 mm or less, metallic powder or dust may be removed after crushing by a vibratory screen or others.

To achieve the above objects, in the cleaning system according to the present invention, a device is provided for cleaning thermoplastic resinous products comprising a vessel and a rotary body built-in in the vessel, wherein the vessel has an entrance port for the thermoplastic resinous products provided in an upper area of one end thereof, an exit port for the thermoplastic resinous products provided in a lower area of the other end thereof, a water supply port and a drainage port; the drainage port being connected to a drainage line for adjusting a water level; the rotary body having a rotary shaft, a screw blade provided on the circumference of the rotary shaft and at least one of a plurality of cleaning plates and cleaning pins; and at least part of the inner surface of the vessel and/or surfaces of at least one of the cleaning plates and the cleaning pins being roughened.

Also, to achieve the above objects, in the cleaning system according to the present invention, a device is provided as another aspect for cleaning thermoplastic resinous products comprising a vessel and agitating blades, wherein the vessel has an entrance port for crushed resinous pieces and a water supply port, both provided in an upper portion thereof, and an exit port for the crushed resinous pieces and a drainage port, both provided in a lower portion provided thereof; a drainage line for adjusting a water level being connected to the drainage port, and at least part of the inner surface of the vessel and/or surfaces of the agitating blades being roughened.

According to the above-mentioned cleaning device, at least part of surfaces to be in contact with the crushed resinous pieces is roughened to effectively scrub or scrape off a surface portion of the crushed resinous piece and sufficiently remove foreign matters such as coated film, plated layer applied to the surface, label or seal adhered to the surface or contaminants. At least part of the inner surface of the vessel and/or a surface of at least one of the screw blade, the cleaning plate and the cleaning pin may be roughened. Preferably, the inner surface of the vessel and a surface of at least one of the screw blade, the cleaning plate and the cleaning pin are roughened. Regarding the screw blade, the cleaning plate and the cleaning pin, a surface of at least one of the screw blade and/or the cleaning plate is more preferably roughened. Also, the inner surface of the vessel and at least part of a surface of the agitator blade is preferably roughened.

If necessary, the cleaning device may be combined with a water rinsing device, a dehydrator, a dryer, a vibratory screen, a wind type classifier and/or a metal sensor to assuredly remove foreign matters such as coated film, label or contaminants and obtain pure crushed resinous pieces. Such crushed resinous pieces may be used in any field requiring the same with no problems.

The above and other objects, effects, features and advantages of the present invention will become more apparent from the following description of embodiments thereof taken in conjunction with the accompanying drawings.

BRIEF DESCRIPTION OF THE DRAWINGS

FIGS. 9A and 9B are a side view and a top view, respectively, of one example of a polymer conveying mechanism provided with an identification device;

FIGS. 11A and 11B are a side view and a top view of another example of a polymer conveying mechanism provided with an identification device;

FIG. 17 is a table showing results obtained by the operation of a crusher;

FIG. 18 is a table showing results obtained by the operation of a identification device; and FIG. 19 is a table showing results obtained by the operation of various cleaning apparatuses.

DETAILED DESCRIPTION OF PREFERRED EMBODIMENTS

Figure 1:
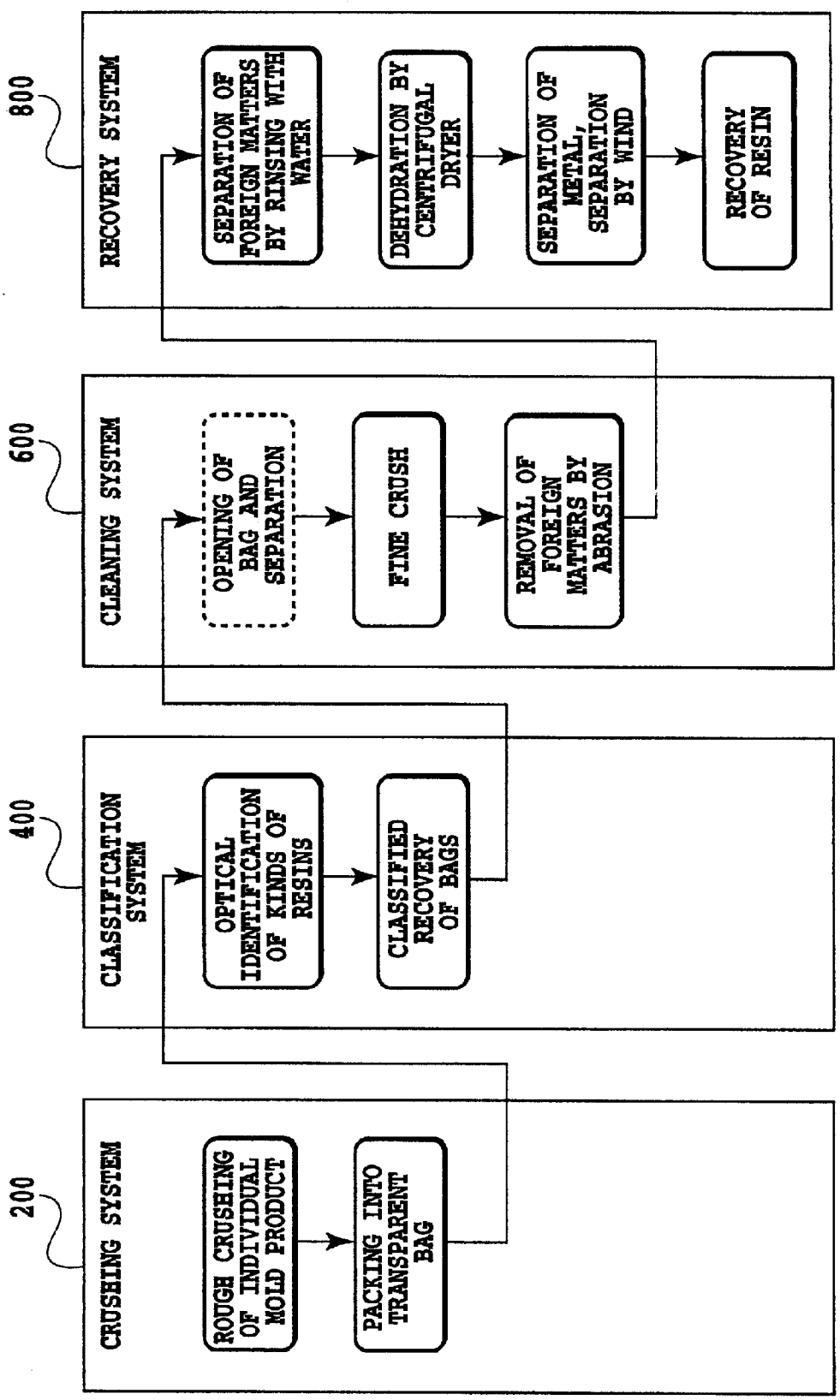
FIG. 1 is a block diagram for schematically illustrating a resin recycling system according to the present invention.

FIG. 1 illustrates one embodiment of a resin recycling system according to the present invention.

The illustrated system includes a crushing system 200, a classification system 400, a cleaning system 600 and a recovery system 800. The crushing system 200 operates to crush resinous mold products one by one into pieces so that 70% or more of the pieces have an equivalent diameter in a range from 1 to 50 mm, and to pack the pieces of every one mold product to one transparent bag. The classification system 400 operates to irradiate light beams to the crushed resinous pieces in the bag, determine a kind of the crushed resin in accordance with the reflected beams therefrom and classify the respective bags into the kinds of resins. The cleaning system 600 operates to clean the crushed resinous pieces taken out from the respective bags classified by the classification system 400 to remove foreign matters on the surface of the crushed resinous pieces. A mechanism for taking out the crushed resinous pieces from the bag and sending the same to a rinsing mechanism may be provided. The recovery system 800 operates to separate the foreign matters from a mixture thereof with the cleaned resinous pieces to recover the crushed resinous pieces.

[1] Crushing System 200 and Classification System 400

Figure 2:
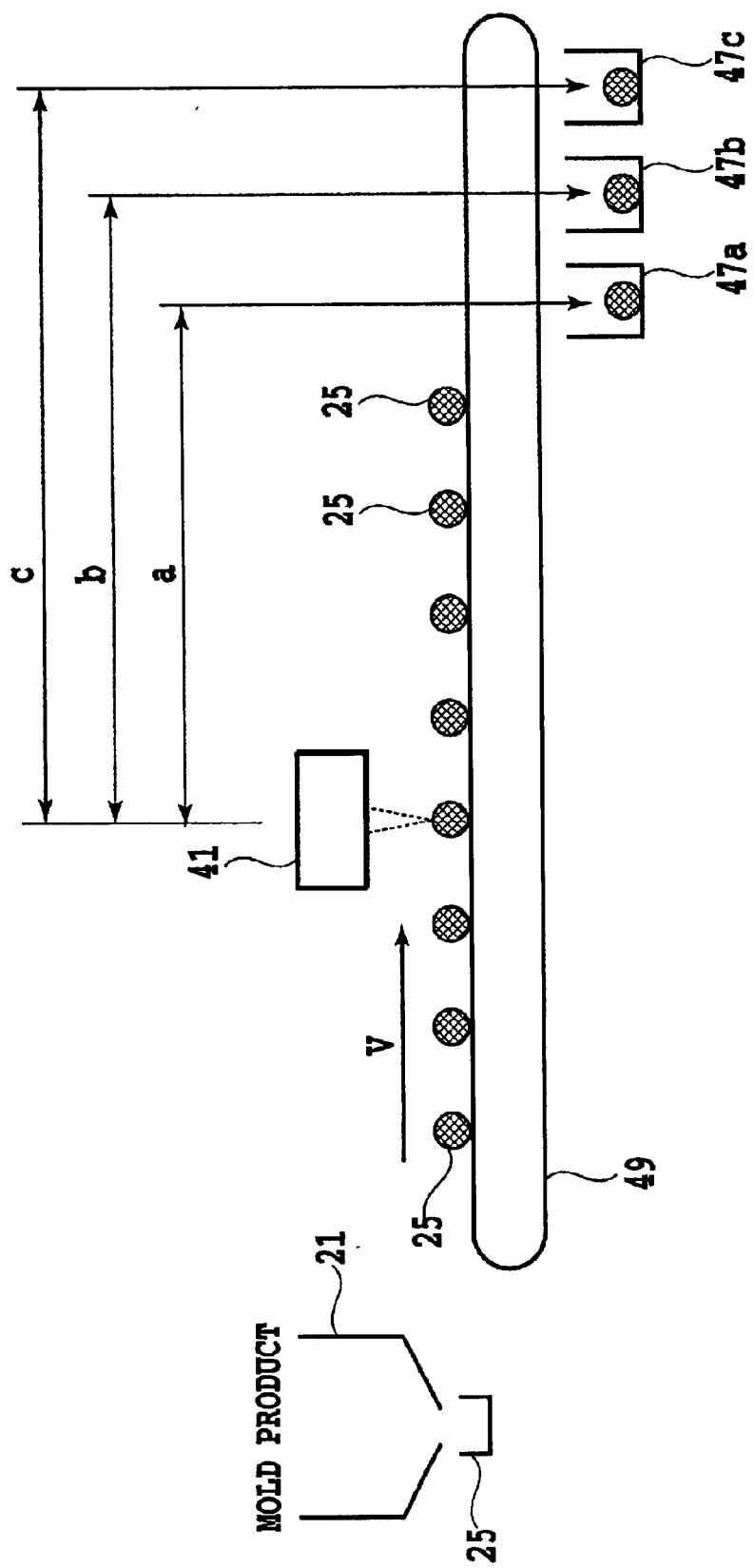
FIG. 2 is a schematic view of one embodiment of crushing means and classifying means used in the present invention.

Initially, the crushing system 200 and the classification system 400 will be described with reference to FIG. 2.

The crushing system 200 has a resin crusher 21. The resinous pieces crushed by the resin crusher 21 are packed in a transparent bag 25 attached at a lower position of the crusher.

As described later, the classification system 400 has a conveyor device 49 for the bags 25, a resin identification device (resin determination device) 41 and classified recovery devices 47a to 47c.

The resin crusher 21 is a device for crushing the resin mold product into pieces so that 70% or more of the pieces have an equivalent diameter in a range from 1 to 50 mm. The resin mold products are crushed into pieces one by one and packed in the bag 25 attached to a lower position of the resin crusher 21. While the resin crusher 21 illustrated in the drawing is of a type carrying out the crushing operation in one step, the operation may be carried out in two steps if the molded product is too large to be introduced into the ordinary size crusher. For example, a crusher for carrying out the coarse crushing and one for crushing the coarsely crushed pieces into smaller pieces having an equivalent diameter in a range from 1 to 50 mm may be provided.

The bag 25 is made of transparent polyethylene and has a size of 23 cm long, 17 cm wide and 40 μm thick. The bag 25 may be opaque and made of other material than polyethylene unless the identification of the crushed resin is disturbed thereby in a resin identification device 41 described later. Also, the bag may be a non-film type.

Figure 3:
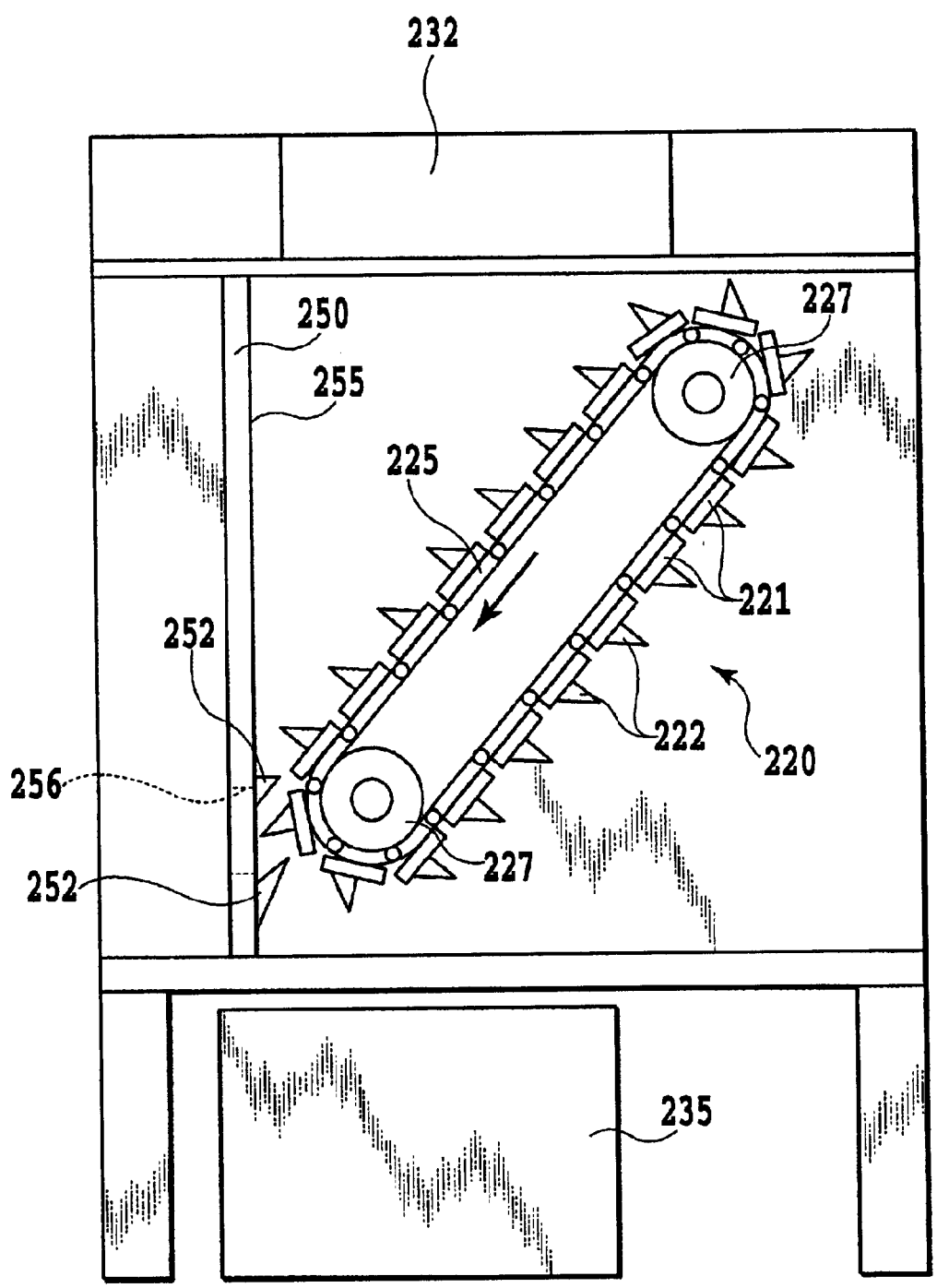
FIG. 3 is a schematic side view of one example of a crusher used in the present invention.
Figure 4:
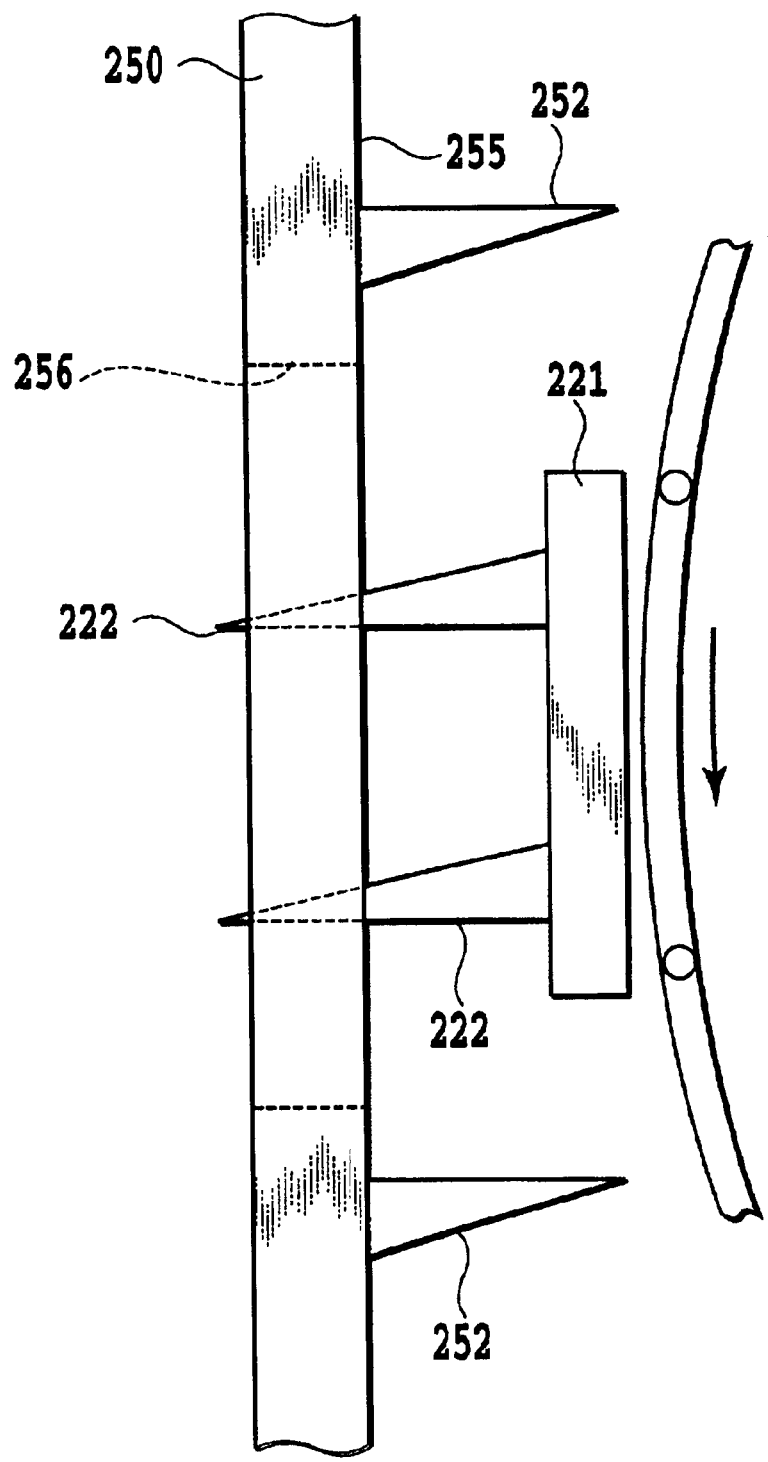
FIG. 4 is an enlarged view of part of FIG. 3.
Figure 5C:
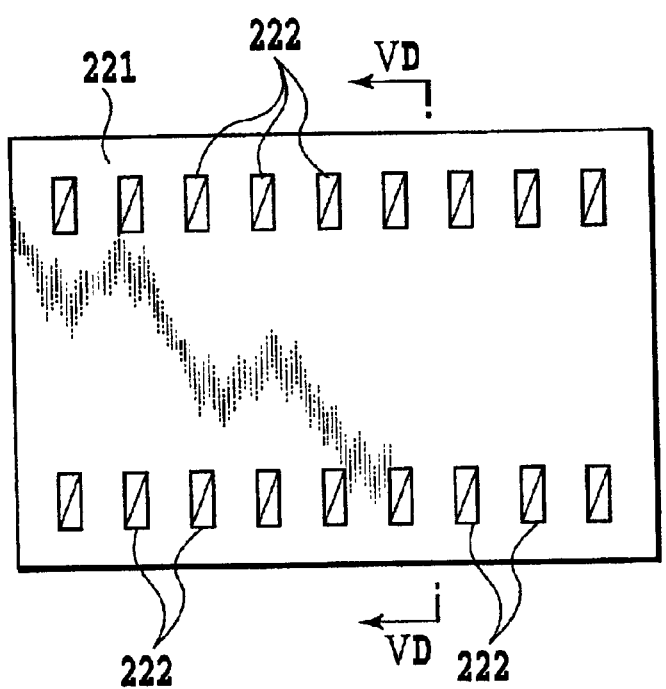
FIG. 5C is a plan view of a connecting plate of a chain conveyor; and 5D is a sectional view taken along a line 5D—5D in FIG. 5C.
Figure 5D:
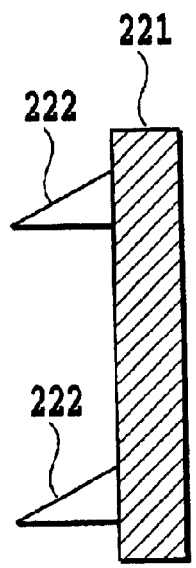
FIG. 5A is a front view of an opposite wall.
FIG. 5B is a sectional view taken along a line 5B—5B in FIG. 5A.
Figure 6A:
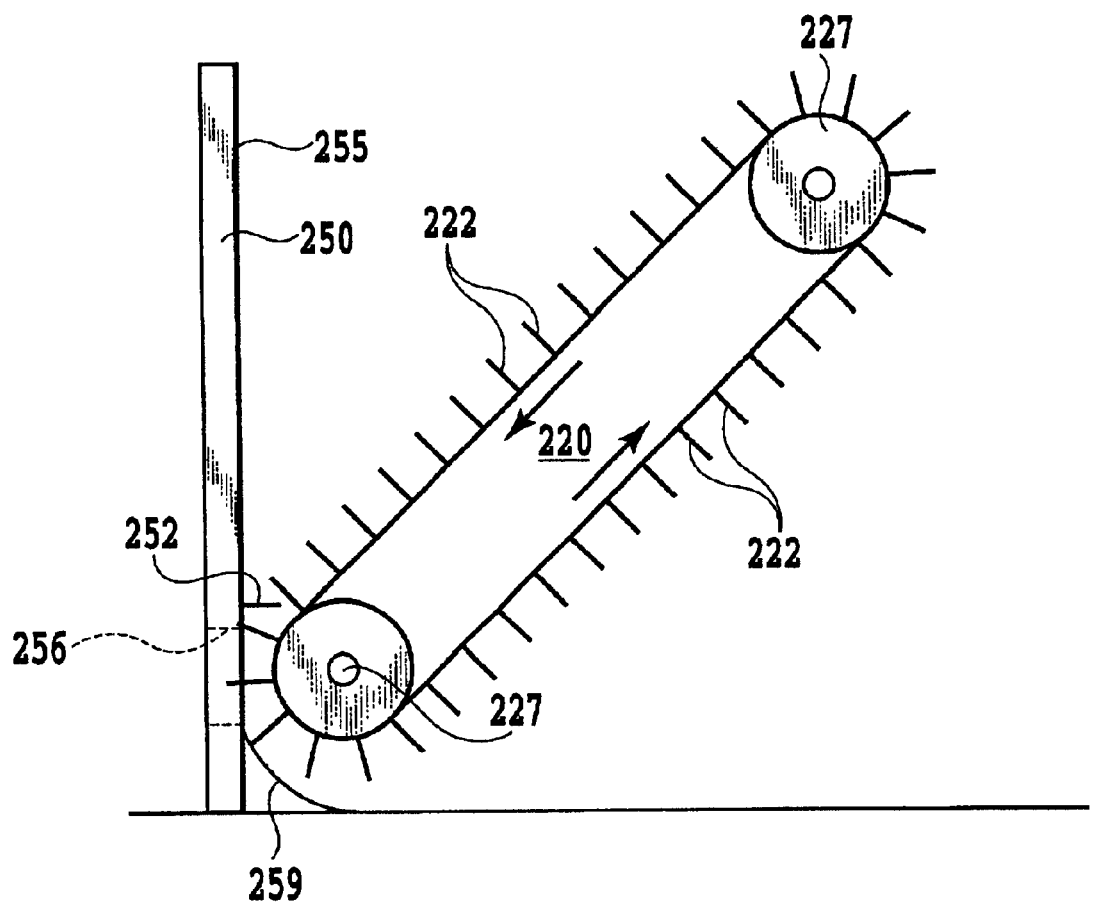
FIG. 6A is a schematic side view of another example of a crusher.
Figure 6B:
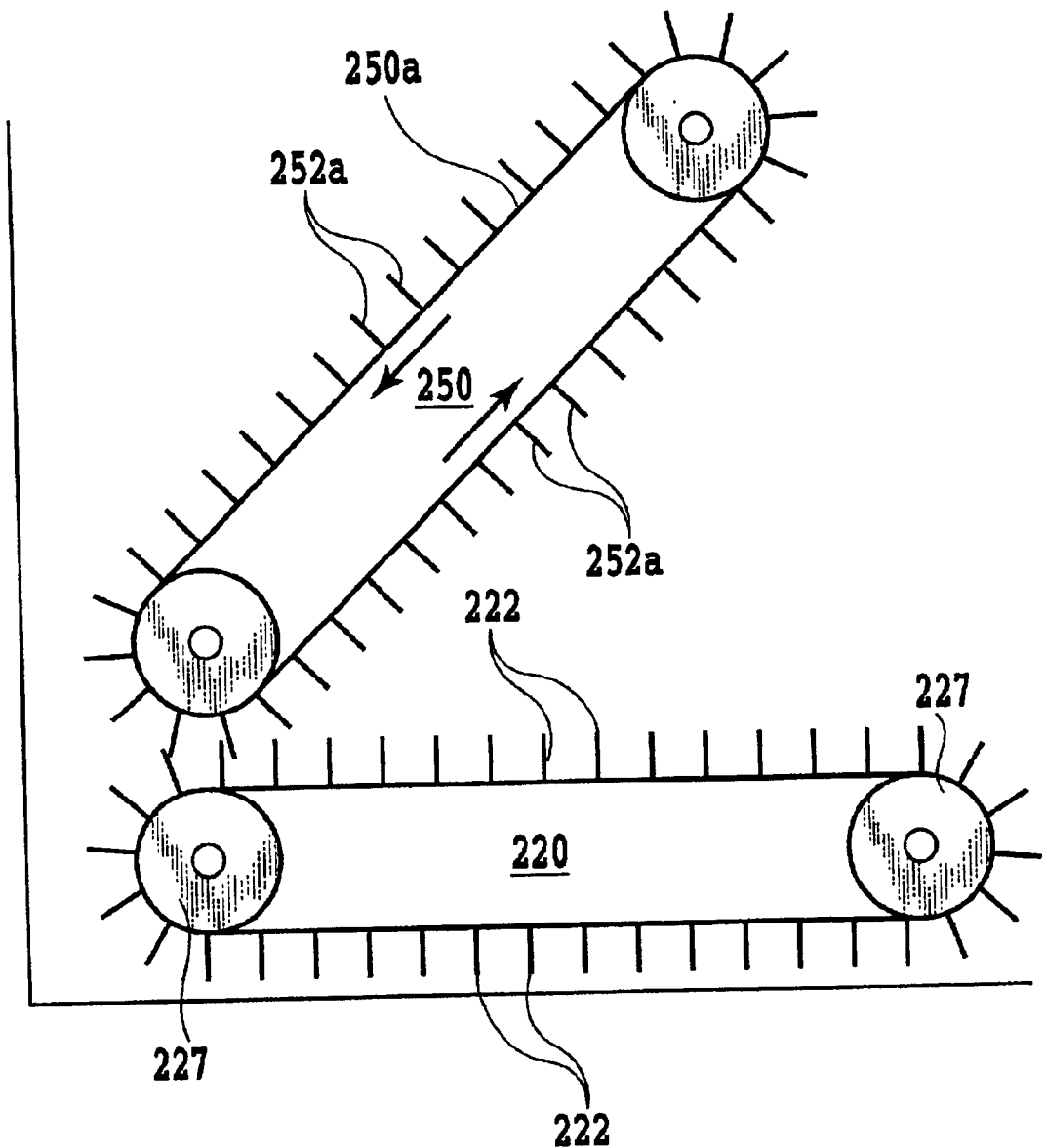
FIG. 6B is a schematic side view of a still further example thereof.

Here, the preferred embodiment of the crusher will be described. FIG. 3 is a schematic side view of one example of a crusher used in the present invention; FIG. 4 is an enlarged view of part of FIG. 3; FIG. 5A is a front view of an opposite wall; FIG. 5B is a sectional view taken along a line 5B—5B in FIG. 5A; FIG. 5C is a plan view of a connecting plate of a chain conveyor; and FIG. 5D is a sectional view taken along a line 5D—5D in FIG. 5C. FIG. 6A is a schematic side view of another example of a crusher; and FIG. 6B is a schematic side view of a still further example thereof.

The crusher illustrated has a chain conveyor (endless conveyor) 220 and an opposite wall (opposite member) 250. The chain conveyor 220 transports articles carried on connecting plates 221 attached to a chain 225 driven by sprockets 227, 227, by displacing the connecting plates 221. This chain conveyor 220 is disposed to have a downward inclination toward the conveying direction indicated by arrow in the drawing to transport the polymer mold products introduced into the crusher from a material introduction port 232 provided at an upper position of the crusher, while carrying the mold products on the connecting plates 221. As shown in FIG. 5C, a plurality of crushing edges 222 (in the drawing, two rows of eighteen edges) are provided on the respective connecting plate 221 of the chain conveyor 220 with sharp ends thereof projecting out of the conveyor. In this regard, instead of the crushing edges 222, crushing pins may be provided.

The opposite wall 250 extends in the vertical direction and has an opposite surface 255 opposed to an end portion of the chain conveyor 220 as seen in the conveying direction (a left end portion in FIG. 3). In the vicinity of a point at which this opposite surface 255 is closest to the chain conveyor 220 (in the vicinity of the lower end in the drawing), a plurality of crushing edges 252 are provided while directing toward the chain conveyor 220. In this regard, instead of the crushing edges 252, crushing pins may be provided. As shown in FIG. 5, the crushing edges 252 on the opposite wall 250 and the crushing edges 222 on the chain conveyor 220 are provided to have different phases from each other not to collide with each other even though both the crushing edges most closely approach. In the opposite wall 250, slits 256 are provided so that tip ends of the crushing edges 222 on the chain conveyor 220 can enter the same not to collide with the opposite wall 250 when the crushing edges 222 most closely approach the opposite wall 250. FIG. 4 illustrates a manner in which the crushing edges 222 of the chain conveyor 220 most closely approach the opposite wall 250 and the tip ends of crushing edges 222 enter the slits 256.

In the crusher thus structured, the polymer mold products introduced from the material introduction port 232 into the crusher and conveyed by the chain conveyor 220 are sheared by the crushing edges 222 and 252 and roughly crushed while being compressed into a zone in which the chain conveyor 220 and the opposite wall 250 are close to each other.

FIG. 6A illustrates a variation of FIG. 3. The crusher shown in FIG. 6A is provided with a guide 259 at a lower end of the opposite wall 250. This guide 259 operates, when the mold product conveyed by the chain conveyor 220 is of a flat-shape and oriented in the vertical direction, to prevent the mold product from escaping from the compression caused by the chain conveyor 220 and the opposite wall 250 and the shearing action of the crushing edges 222, 252 and falling down while not being crushed.

In this regard, while the crushing edges are provided both in the chain conveyor 220 and the opposite wall 250 in the embodiments shown in FIGS. 3 and 6A, they may be provided in at least one of the both. However, if they are provided in both of them, the shearing action of the crushing edges is more enhanced.

In a crusher shown in FIG. 6B, two chain conveyors 220 and 250a are provided so that a distance between the both becomes gradually smaller in the conveying direction. According to this crusher, the upper inclined chain conveyor 250a has a function as the opposite member. The crushing edges 222 and 252a of the respective conveyors 220 and 250 are provided to have different phases from each other not to collide with each other even though both the crushing edges most closely approach While two chain conveyors 220, 250a have crushing edges 222, 252a, respectively, in the embodiment shown in FIG. 6B, these may be provided on at least one of the conveyors. If the crushing edges are provided on both the conveyors, the shearing operation of the crushing edges can be more assuredly carried out. In the arrangement shown in FIG. 6B, the upper chain conveyor 250a may be replaced with a slanted opposite wall having the same inclination as the conveyor 250a. Alternatively, rollers may be provided. That is, it is sufficient that there is an arrangement for transporting the polymer mold products by the conveyor means and pushing the same into a gap between the conveyor means and the opposite member so that the mold products are roughly crushed while being compressed by the crushing edges or pins.

In this regard, a continuous system may be arranged from the arrangement shown in FIG. 3 or 6 by providing a fine crusher (for more finely crushing the coarsely crushed pieces) subsequent thereto.

Now return to FIG. 2 wherein the conveyor device 49 transports the bags in which the crushed resinous pieces are packed at a predetermined speed V and stops the same if necessary. If it is expected that a more time is required for the identification of resin, for example, because of a slow calculating speed of the resin identification device 41 (described later), the stop of the conveyor device will be necessary. The conveyor device 49 may include a conveyor with trays and if an expected arrival time has been reached, the corresponding tray is inclined to throw down the bag carried thereon into a recovery box beneath the same. The expected arrival time is a time instant obtained by adding a time period necessary for a certain bag in which a resin of kind A are packed to be conveyed to a recovery box for the resin A to a time instant at which the resin in the bag has been identified as A. The corresponding tray is a tray on which the certain bag is placed. In this regard, while the crusher 21 and the conveyor device 49 (and the resin identification device 41 or others) are provided in the same factory in FIG. 2, the both may be provided in different factories, respectively, such that the resinous pieces crushed by the crusher 21 and stuffed in the bag 25 are transported to the factory in which the conveyor device 49 or others is provided. In other words, even in such an arrangement, it is possible to suppress the transportation cost to a lower level because the resin is reduced in volume.

The resin identification device 41 is a device for identifying a kind of the crushed resinous pieces in the bag 25 based on a Raman spectrum analysis. That is, a laser beam is irradiated to the crushed resinous pieces in the bag 25 which passes a detection position (identification position) (or is made to stop for a while if a time period is required for the identification), and reflected therefrom. A Raman spectrum is obtained from the reflected beam and sequentially compared with Raman spectra of known resins to find the coincidence of Raman spectra of both the resins to decide a kind of resin in the bag. For this purpose, the resin identification device 41 stores Raman spectra of various resins obtained in advance.

The classified recovery device 47a is for a resin A. Similarly, the classified recovery device 47b is for a resin B, and the classified recovery device 47c is for a resin C. If there are four kinds of resins or more, the number of classified recovery devices may be correspondingly increased. A distance between the classification/recovery position of the classified recovery device 47a and the detection position of the resin identification device 41 is a; a distance between the classification/recovery position of the classified recovery device 47b and the detection position of the resin identification device 41 is b; and a distance between the classification/recovery position of the classified recovery device 47c and the detection position of the resin identification device 41 is c. When a current time reaches the expected arrival time, the classified recovery device corresponding to the kind of resin in correspondence to that expected arrival time is operated to recover the bag located at the classification/recovery position of that classified recovery device into the recovery box.

The classified recovery device is not limited to the illustrated one in which a tiltable tray of the conveyor is inclined to throw down the bag into the recovery box disposed beneath the conveyor. For example, a manipulator may be provided above the conveyor and lift the bag on the conveyor to recover the same. Alternatively, a pusher may be provided for pushing the bag on the conveyor aside by a rod or the like. Or, the classified recovery devices may not be individually provided in correspondence to kinds of resins, but all the bags may be recovered by a single recovery device, from which the bags are distributed into the respective recovery boxes in correspondence to the kinds of resins.

Figure 7:
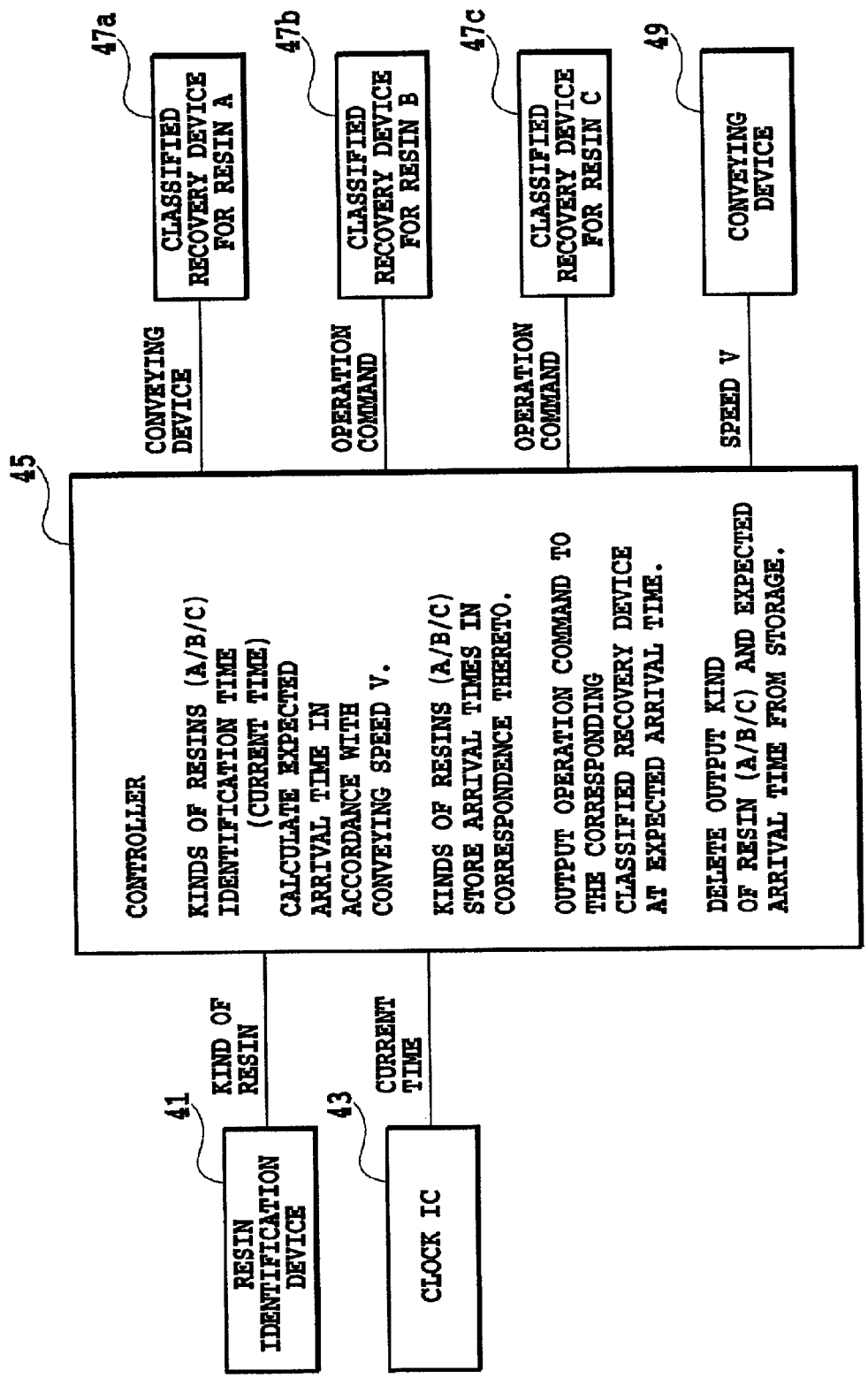
FIG. 7 is a block diagram illustrating the relationship between inputs and outputs of a controller for the system shown in FIG. 2.
Figure 8:
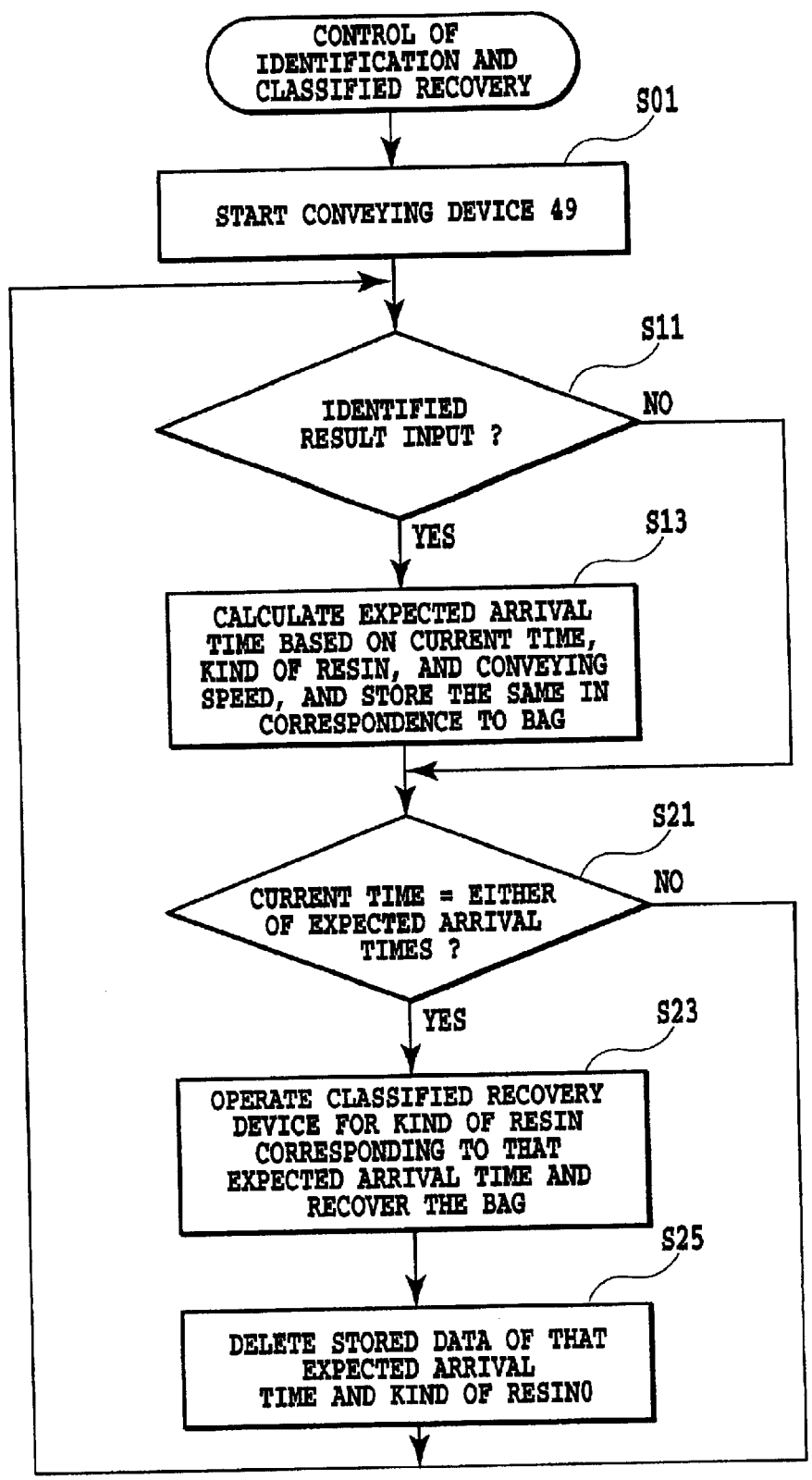
FIG. 8 is a flow chart illustrating one example of a procedure for controlling the identification and classification/recovery of resins.

FIG. 7 is a block diagram illustrating the relationship between inputs and outputs of a controller for the system, and FIG. 8 is a flow chart illustrating a procedure for controlling the identification and classification/recovery of resins. The description will be made below with reference to FIGS. 7 and 8.

First, the conveyor device 49 starts (S01).

When the identification result (a kind of resin in the bag 25 passing through the identification position or stopping in a period necessary for the identification at the identification position) is input from the resin identification device 41 (i.e., the answer is YES at S11), the expected arrival time at which the bag (packing the identified resin) reaches the classified recovery device (for example, the device 47a) is calculated based on a current time obtained from a clock IC 43, a distance to the classified recovery device determined in accordance with a kind of the identified resin (if the identified resin is a kind A, this distance is a to the classified recovery device 47a) and a conveying speed V of the conveyor device 49, and stored in a memory (not shown) within a controller 45 in correspondence to the resin kind A (i.e., to the classified recovery device 47s) (S13). In this regard, since the conveying speed V and the distance (a/b/c) are known, a time period necessary for the transportation determined in accordance with kinds of resins may be added to the current time, instead of carrying out the above calculation.

If the current time reaches either one of the expected arrival times stored in the memory (not shown) of the controller 45 (i.e., if the answer is YES at S21), an operation command is issued from the controller 45 to the classified recovery device stored in correspondence to this expected arrival time. Thereby, the above-mentioned classified recovery device is operated to recover the bag located at the classification/recovery position of the classified recovery device (S23). Thereafter, the expected arrival time and data of the classified recovery device stored in correspondence thereto are deleted from the memory (S25).

Other preferred embodiments of the resin identification device will be described in more detail below with reference to FIGS. 9 to 11.

(1) First Embodiment

Figure 10:
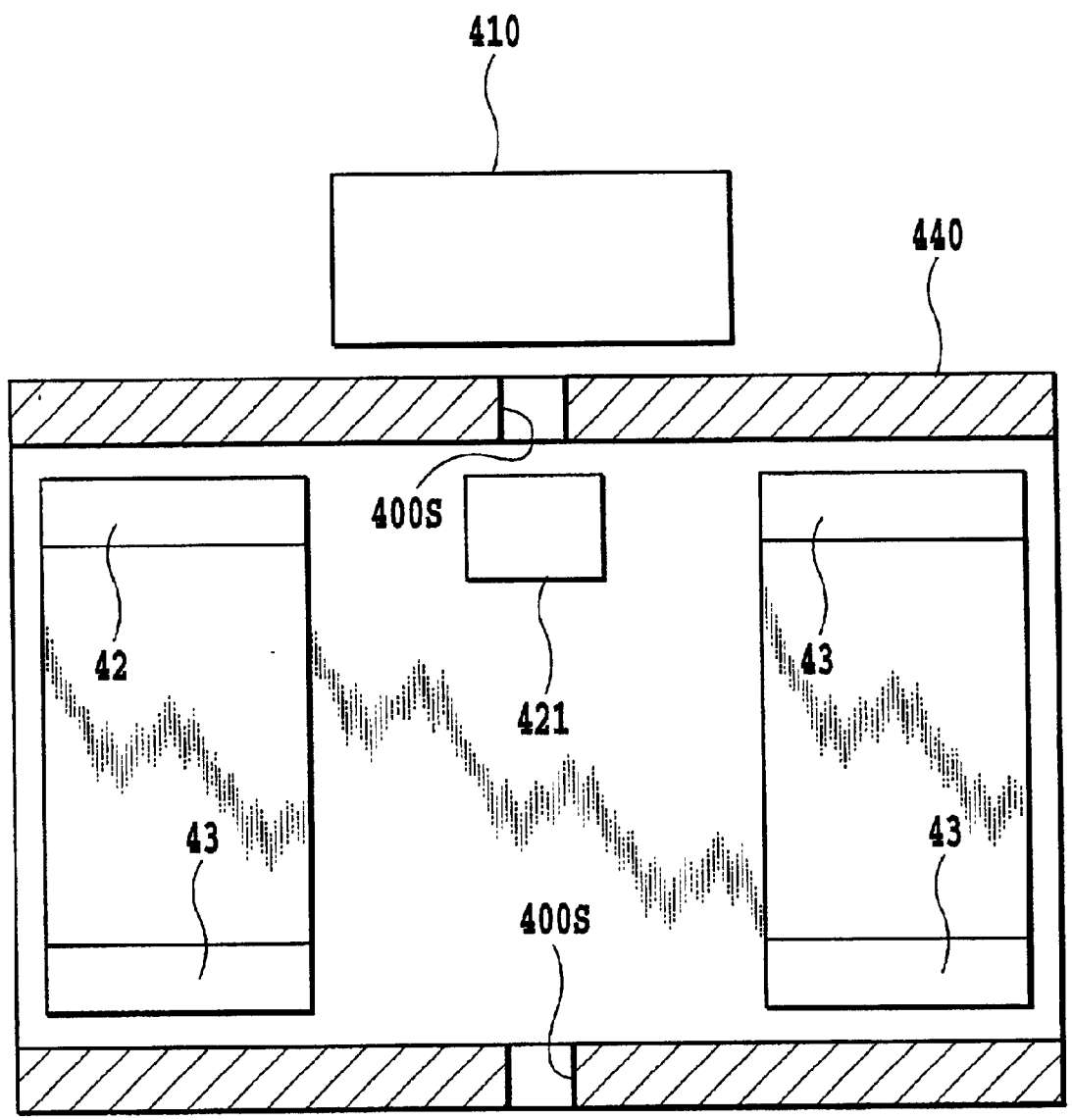
FIG. 10 is a sectional view taken along a line 10—10 in FIG. 9A.

FIGS. 9A, 9B and 10 schematically illustrate a first embodiment of a polymer conveying mechanism provided with an identification device, wherein FIG. 9A is a side view, FIG. 9B is a top view and FIG. 10 is a sectional view taken along a line 10—10 in FIG. 9A. In the drawings, reference numeral 410 denotes a polyethylene bag (having a size of 23 cm long, 17 cm wide and 40 $\mu$m thick) in which resin pieces crushed to have a suitable size (for example, so that 70% or more of the pieces have an equivalent diameter in a range from 1 to 50 mm) are packed, wherein the equivalent diameter is a diameter of a circle having the same area as a projected area of an object.

The bag 410 is conveyed on a conveyor belt 440 driven by drive rollers 441, 441 in the arrowed direction, and irradiated with a laser beam from a sensor element 421 in the midway of its travel, whereby a Raman scattering can be detected. The detected signal is fed to an identification and calculation device 420 in which a kind of resin is identified. That is, the detected Raman spectrum is sequentially compared with those of various known resins stored in advance until the known resin coinciding with the resin to be identified is found. Based on the identification result, a timing for a dispensing operation is calculated and a dispensing device 430 is operated at the calculated timing. Thereby, the bag 410 is removed from the conveyor belt 440 and put into a vessel in correspondence to a kind of the identified resin (either one of vessels 435a, 435b and 435c). The dispensing timing is a timing at which the bag 410 of which the Raman scattering has been detected at a position of the sensor element 421 to identify the kind of resin reaches the vessel (either one of vessels 435a, 435b and 435c) corresponding to the kind of resin packed in the bag.

According to the first embodiment, as illustrated, a plurality of slits 400S of a predetermined length used as a light window for allowing a light beam to pass through the same (having a size of 10 mm wide and 20 cm long) are arranged along a center portion of the width of the conveyor belt 440 at a predetermined pitch in the belt-running direction. The above-mentioned sensor element 421 is disposed at a position in correspondence to the slit position beneath the conveyor belt 440 in the vicinity of the inner surface of the conveyor belt 440. Thus, it is possible to maintain a distance between the light-receiving part of the sensor element 421 and the bottom surface of the bag 410 always at a predetermined short distance (for example, approximately 10 mm) capable of detecting the Raman scattering, irrespective of shapes of the bags 410. Thereby, the high-precision resin identification can be carried out.

In this regard, a member for pressing the bag 410 onto the upper surface of the conveyor belt 440 may be provided at a position above the sensor element 421 to prevent the bottom surface of the bag 410 from floating upward from the upper surface of the conveyor belt 440, so that the above-mentioned distance between the light-receiving part of the sensor element 421 and the bottom surface of the bag 410 is maintained constant.

(2) Second Embodiment

FIG. 11 schematically illustrates a second embodiment of a polymer conveying mechanism wherein FIG. 11A is a side view and FIG. 11B is a top view. In the drawings, the same reference numerals are used for denoting the same or similar parts as those in FIG. 9, and the explanation thereof will be eliminated.

According to the second embodiment, as illustrated, a window plate 422 having a light window for allowing a light beam to pass through the same is disposed at a position on the lateral side of a conveyor belt 440a, and is also used as a stopper member. A sensor element 421 is provided at a position on a side of the window plate 422 opposite to the conveyor belt 440a so that the light receiving part of the sensor element 421 confronts the window plate 422. At a position opposite to the window plate 422, a plate-like curved guide 423 is provided directly above the conveyor belt 440a, while interposing the conveyor belt between the window plate and the curved guide. This guide 423 operates to push the bag 410 transported on the conveyor belt 440a toward the window plate 422 and cause the bag 410 to be in contact with the window plate 422. According to this structure, it is possible to maintain a distance between the light-receiving part of the sensor element 421 and the lateral surface of the bag 410 at a thickness of the window plate 422 (for example, approximately 10 mm), irrespective of shapes of the bags 410. In other words, it is possible to maintain the distance at a value as small as capable of detecting the Raman scattering. Thereby, the high-precision resin identification can be carried out.

Instead of the guide 423 formed of a curved plate as in the illustrated embodiment, one or two rollers or more may be used for the same purpose. In such a case, the roller may be either a freely rotatable type or one driven to rotate in synchronism with the conveyor belt 440a.

While an endless belt is used as a conveyor means in the above-mentioned embodiment, the conveyor means according to the present invention should not be limited to the endless belt, provided it is capable of transporting the polymer to be detected while maintaining a predetermined short distance between the light-receiving part of the sensor element 421 and the polymer. For example, the conveyor means may be of a type for transporting the bag 410 carried on a tray.

[2] Rinsing System 600

Next, the cleaning system 600 will be described.

Figure 12:
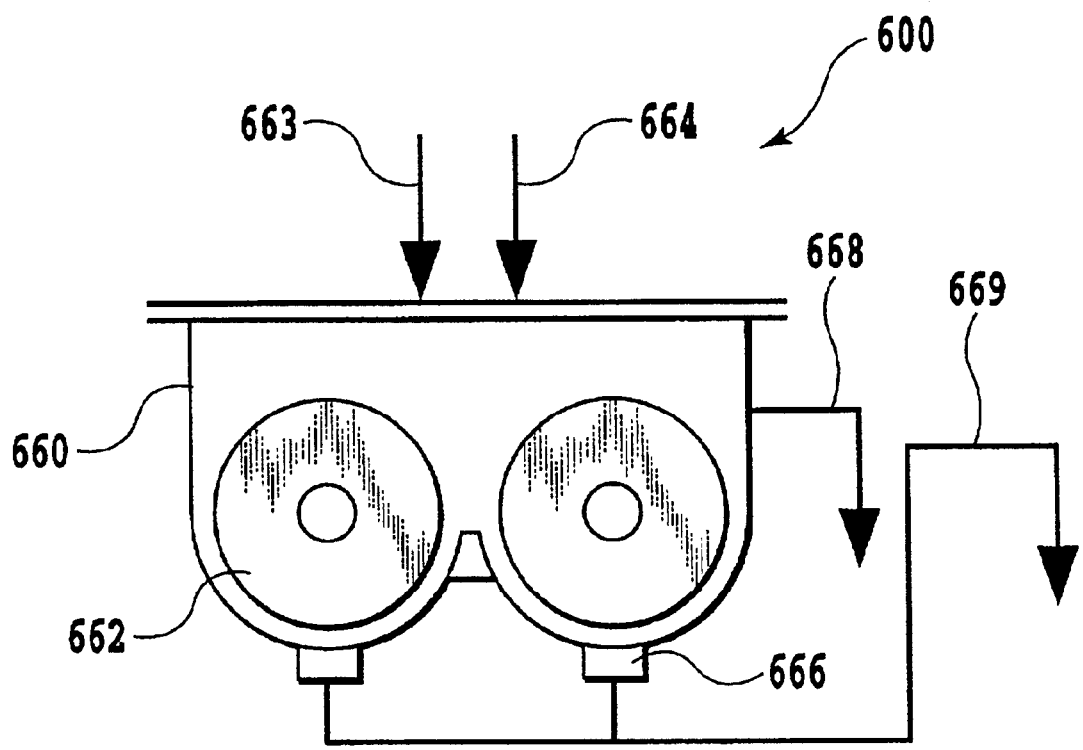
FIG. 12 is a cross-sectional view of one example of a horizontal type continuous cleaning apparatus according to the present invention.
Figure 13:
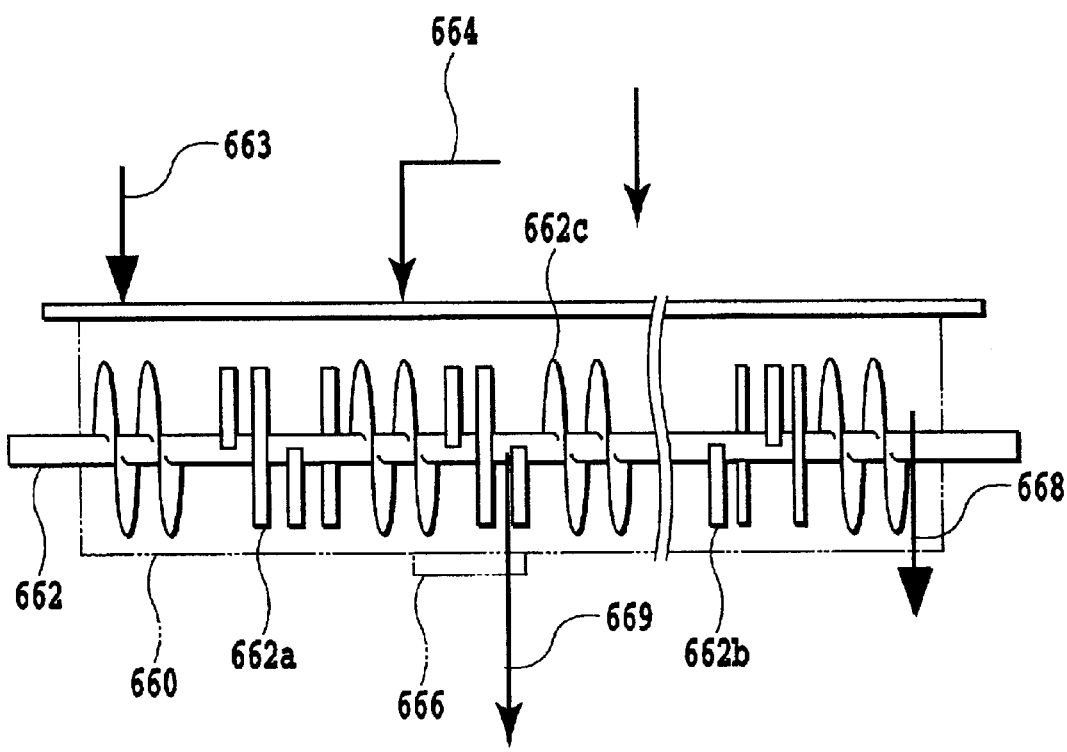
FIG. 13 is an elevational sectional view of one example of a horizontal type continuous cleaning apparatus according to the present invention.
Figure 14:
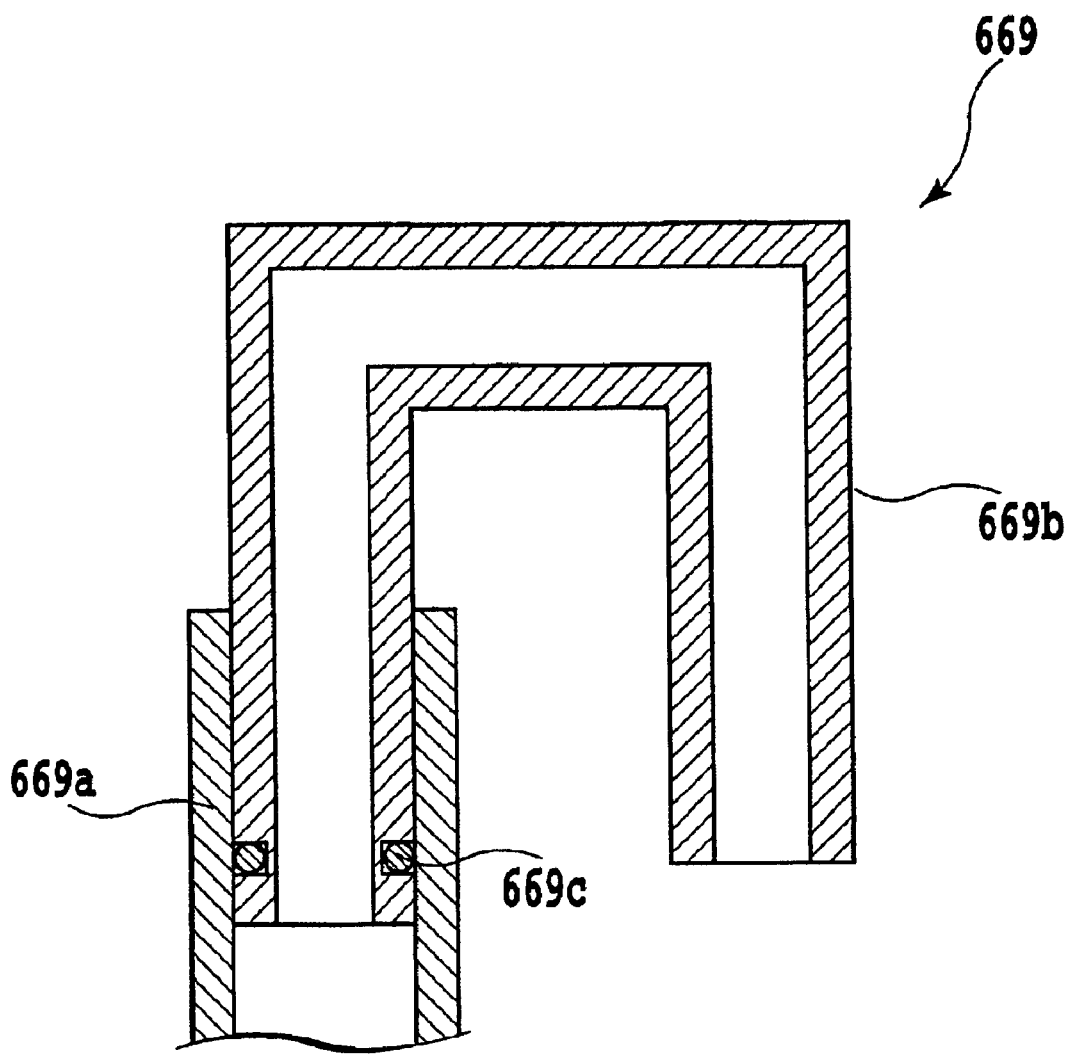
FIG. 14 is a sectional view illustrating a drainage line for adjusting a water level of a cleaning apparatus.

FIGS. 12 to 14 illustrate a structure of the continuous cleaning device 600, wherein FIG. 12 is a schematic cross-sectional view, FIG. 13 is a schematic side sectional view and FIG. 14 is a detailed illustration of a drainage line 669 for adjusting a water level.

The continuous cleaning device 600 has a vessel 660 and rotary bodies 662. In FIGS. 12 and 13, the vessel 660 may be formed of a metal such as stainless steel. An entrance port 663 for crushed resinous pieces is provided at one end of an upper wall of the vessel 660, and an exit port 668 for the crushed resinous pieces is provided in a lateral wall on the opposite end side. A water feeding port 664 is provided at at least one position of the upper wall of the vessel 660, and a drainage port 666 is provided at at least one position of the lower wall of the vessel 660. A drainage line 669 for adjusting a water level is connected to the drainage port 666.

A predetermined amount of crushed resinous pieces is continuously introduced into the vessel 660 through the entrance port 663, conveyed along the same and discharged from the exit port 668. In this process, preferably, the introduction speed and the discharge speed of the crushed resinous pieces are approximately equal to each other and maintained roughly constant. A feeding speed of water to be supplied from the water feeding port 664 is preferably controlled so that a water level determined by the water level adjusting pipe 669b is maintained, while taking a draining speed of water from an open end of the water level adjustment drainage line 669 into account. By adjusting the introduction and discharge speeds of the crushed resinous pieces and those of water, constant amounts of crushed resinous pieces and water are always conveyed through the vessel 660. Accordingly, the crushed resinous pieces are evenly cleaned and, as a result, the surfaces of the crushed resinous pieces are free from the foreign matters left thereon, and prevented from being excessively scraped off.

In the drainage port 666 provided in the bottom wall or others of the vessel 660, slits or punched plate are disposed. Also, in the drainage port 666, the water level adjustment drainage line 669 is connected. The water level adjustment drainage line 669 has a drainage pipe 669a connected to the drainage port 666 and standing upward on the lateral side of the vessel 660 and a water level adjustment pipe 669b fitted to the interior of the drainage pipe 669a in a slidable manner. Between the inner surface of the drainage pipe 669a and the outer surface of the water level adjustment pipe 669b, an O-ring 669c is interposed to keep the water-tight sealing. By moving the water level adjustment pipe 669b upward and downward, it is possible to adjust the water level in the cleaning device 600 and maintain a predetermined water level.

While the water feeding port 664 and the drainage port 666 are provided at one position, respectively, in the illustrated embodiment, they may be provided at a plurality of positions, respectively. When the water feeding ports 664 are provided at a plurality of positions from one end to the other end of the vessel 660, it is possible to quickly guide dust or others generated by the cleaning operation to the drainage ports 666 and drain the same outside through the water level adjustment line 669. Further, it is also possible to prevent the dust or others from sticking again to the crushed resinous pieces.

Openings provided in the drainage port 666 such as slits or holes of a punched plate have a size to allow water or dust to pass through the same but prevent the crushed resinous pieces from passing. The slit is preferably of a size in a range from approximately 0.3 to 2 mm in view of the mechanical strength. While the drainage port 666 may be provided in either of the bottom wall or the lateral wall, the bottom wall is preferable in view of the adjustment of the water level. In this regard, if the drainage port is provided in the lateral wall, the position thereof is preferably as low as possible, of course.

An open end of the water level adjustment pipe 669b opens to the atmosphere so that the water level in the vessel 660 is generally equal to a height of the open end of the water level adjustment pipe 669b. Thereby, even if the feed rate of water varies, the water level is maintained constant and excessive water is drained from the open end of the water level adjustment pipe 669b. The drained water may be accumulated in a tank and reused after being pumped up and filtrated through a filter to remove dust or others therefrom.

The rotary shaft 662 is provided with screw blades 662c for cleaning the crushed resinous pieces while conveying the same from the entrance port 663 to the exit port 668, and cleaning plates 662a and cleaning pins 662b for scrubbing or scraping off foreign matters from the surface of the crushed resinous pieces while imparting shock thereto, all of which are alternately arranged. Either one of the cleaning plate 662a or the cleaning pin 662b may be eliminated, although the combined use thereof is preferable.

A diameter of the screw blade 662c, a thickness of the cleaning plate 662a and a length of the cleaning pin 662b are not limited, provided the efficient cleaning is achievable. The screw blades 662c may have a generally equal diameter; the cleaning plates 662a may have generally equal diameter and thickness; and the cleaning pins 662b may have a generally equal length. Also, the number of screw blades 662c for cleaning the crushed resinous pieces while conveying the same is preferably two or three per one zone. An axial length of the screw blade 662c per one zone is preferably 0.5 to 3 relative to a diameter. While these screw blades 662c, the cleaning plates 662a and the cleaning pins 662b are alternately arranged, the number thereof disposed in one zone may be equal in all zones or different from those of other zones.

A pitch of the screw blades 662c must be determined by taking a rotational speed of the rotary shaft into account. Since the rotary shaft is necessarily made to rotate at a relatively high speed for effectively abrading and cleaning the crushed resinous pieces, the pitch is preferably in a range from 0.3 D to 1.5 D wherein D represents a diameter of the screw blade 662c. If the pitch is less than 0.3 D, a gap between adjacent two screw blades is so small that the crushed resinous pieces may be caught in the gap and rotate together with the screw blades to disturb the transportation or the cleaning. Also, the crushed resinous pieces caught in the gap may melt to disable the continuation of cleaning operation. On the other hand, if the pitch exceeds 1.5 D, the conveying efficiency is lowered. In this regard, when the conveying efficiency of the screw blade 662c is excessively large and thus a dwell time of the crushed resinous pieces becomes insufficient in the area wherein the cleaning plates 662a or the cleaning pins 662b are provided, part of the screw blade may be cut off so that a balance is adjustable between the conveying capacity and the cleaning operation.

Shapes of the cleaning plate 662a are not limited. For example, the cleaning plate may be circular or polygonal, such as triangular or quadrangular, as seen in the axial direction of the rotary shaft 662. The cleaning plate 662a is not necessarily symmetric in shape with respect to the rotary shaft 662. Also, it may be slanted to the rotary shaft 662 to have a conveying function. The cleaning plates inclined in the conveying direction and in the opposite direction thereto may be combined with each other to enhance the cleaning efficiency. The same is true to the cross-sectional shape of the cleaning pin 662b, which may be circular or polygonal such as triangular or quadrangular. The polygonal cross-section is favorable because the cleaning efficiency becomes higher. The cleaning pin 662b is not necessarily projected vertical to the circumference of the rotary shaft 662 but may be inclined at a proper angle.

The rotational speed of the rotary shaft 662 has a proper range variable in accordance with sizes of devices, kinds of crushed resinous pieces or degrees of cleaning demanded. Generally, a linear speed of a tip end of the cleaning plate 662a or the cleaning pin 662b is preferably in a range from 0.5 to 20 m/sec, more preferably from 1 to 10 m/sec. In the rotational speed under which the linear speed is less than 0.5 m/sec, it is impossible to sufficiently clean the surface of the crushed resinous piece even if the treatment time is prolonged. Contrarily, if the linear speed exceeds 20 m/sec, the interior temperature of the cleaning device rises to soften and be liable to melt the crushed resinous pieces, which is unfavorable because a large driving power is necessary.

At least part of surfaces to be in contact with the crushed resinous pieces; that is, the inner surface of the vessel 660 and surfaces of the screw blade 662c, the cleaning plate 662a and the cleaning pin 662b; is roughened to constitute an abrasive surface. Accordingly, the foreign matters on the surface of the crushed resinous piece can be efficiently scrubbed or scraped off. A depth of the irregularity on the roughened surface is preferably in a range from 40 to 2000 $\mu$m, more preferably from 50 to 1000 $\mu$m, most preferably from 60 to 500 $\mu$m. If the depth is less than 40 $\mu$m, the foreign matters could not be sufficiently removed. On the other hand, if exceeding 2000 $\mu$m, the surface of the crushed resinous piece is excessively scraped off to unfavorably lower the recovery percentage of resin. A degree of the above-mentioned surface-roughening is not necessarily constant from the entrance port 663 to the exit port 668. The cleaning efficiency may be adjustable, for example, by changing the roughening degree to be coarser toward the entrance port 663 and relatively smoother toward the exit port 668. Also, the cleaning efficiency may be enhanced, for example, by mixing various abradants with water.

While a two-shaft type cleaning device is illustrated in the drawing, this is merely one example and a single-shaft type or a multi-shaft type including a three- or more shaft type may be adopted. When the single-shaft type is adopted, however, the movement of the crushed resinous pieces becomes monotonous in the device to lower the cleaning efficiency. Contrarily, the device having three shafts or more is complicated in structure and expensive.

An interior space of the cleaning device may be suitably designed in accordance with throughputs or others thereof. An interior dimension of the vessel 660 in the direction vertical to the rotary shaft 662 may be suitably selected in accordance with a diameter of the screw shaft 662c and a necessary gap between the inner surface of the vessel 660 and a tip end of the screw blade 662c. An axial dimension of the rotary shaft 662 is 5 to 30 times, preferably 10 to 30 times a diameter of the screw blade 662c.

If the axial dimension is less than five times the diameter of the screw blade 662c, the crushed resinous pieces are conveyed to the exit port 668 with part of them being not sufficiently cleaned, which degrades the quality of recycled resin material due to the mixture of the insufficiently cleaned crushed resinous pieces. If the axial dimension exceeds 30 times the diameter of the screw blade 662c, the mechanical strength of the rotary shaft 662 must be increased or a support system thereof must be changed, which makes it difficult to prevent the inner surface of the vessel 660 from coming in contact with the screw blade 662c or others and increases a cost of the device to a great extent.

Figure 15:
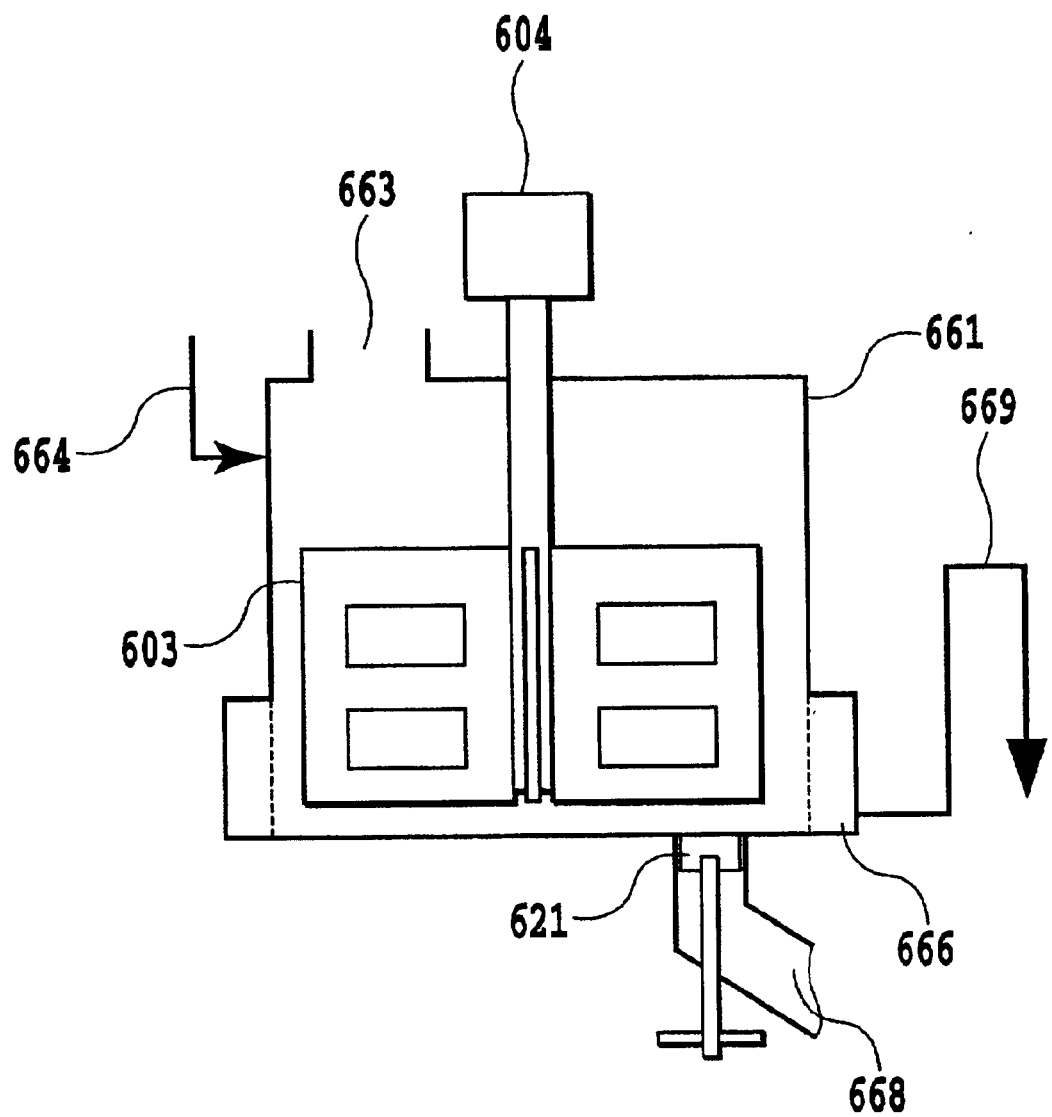
FIG. 15 is a cross-sectional view illustrating one example of a vertical and batch type cleaning apparatus according to the present invention.

While the above description has been made on a continuous type cleaning device, a batch type may be adopted. FIG. 15 illustrates a batch type cleaning device of a vertical type as one example thereof.

A vessel 661 is preferably cylindrical and formed of a metal such as stainless steel. An entrance port 663 for introducing crushed resinous pieces is provided on the upper surface of the vessel 661, and an exit port 668 for discharging the crushed resinous pieces is provided on the bottom surface thereof. A piston-shaped valve 621 is provided in the exit port 668, so that the valve is flush with the bottom surface of the vessel body when the valve is closed. After the cleaning has completed, the piston-shaped valve 621 is opened to take the crushed resinous pieces out of the vessel.

On the lateral surface of the vessel 661, a water supply port 664 is provided at an upper position and a drainage port 666 is provided at a lower position. A water level adjustment drainage line 669 shown in FIG. 14 is connected to the drainage port 666. Alternatively, the water supply port 664 may be provided on the upper surface of the vessel 661, and the drainage port 666 may be provided on the lower surface of the vessel 661. While the drainage port 666 is formed throughout a lower area of the lateral surface of the vessel 661 in FIG. 15, it may be provided on part of the lower area of the lateral surface. Further, there is no limitation in positional relationship between the entrance port 663 and the exit port 668, but they are preferably provided on a diagonal of the cross-section of the vessel 661. If so, all the crushed resinous pieces are evenly and efficiently cleaned.

There is no limitation in shape of an agitator blade 603, but a paddle type blade or a lattice type blade having a large surface area is preferably used. The agitator blades 603 are arranged at a center of the vessel 661, and at least part of the inner surface of the vessel 661 and the surface of the agitator blade is roughened. A degree of this roughening, a ratio between the crushed resinous pieces and water and a size of openings such as slits or holes of a punched plate provided in the drainage port 666 are similar to those in the above-mentioned horizontal type continuous cleaning device.

[3] Recovery System 800

Then, the description will be made on the recovery system 800.

The recovery system 800 operates to separate foreign matters from a mixture of the foreign matters and crushed resinous pieces cleaned by the cleaning system 600 and recover the crushed resinous pieces. The recovery system 800 may include various systems; for example, a system for removing metallic material by using magnetic force, a system for removing foreign matters by rinsing and a system for removing foreign matters with wind.

Figure 16:
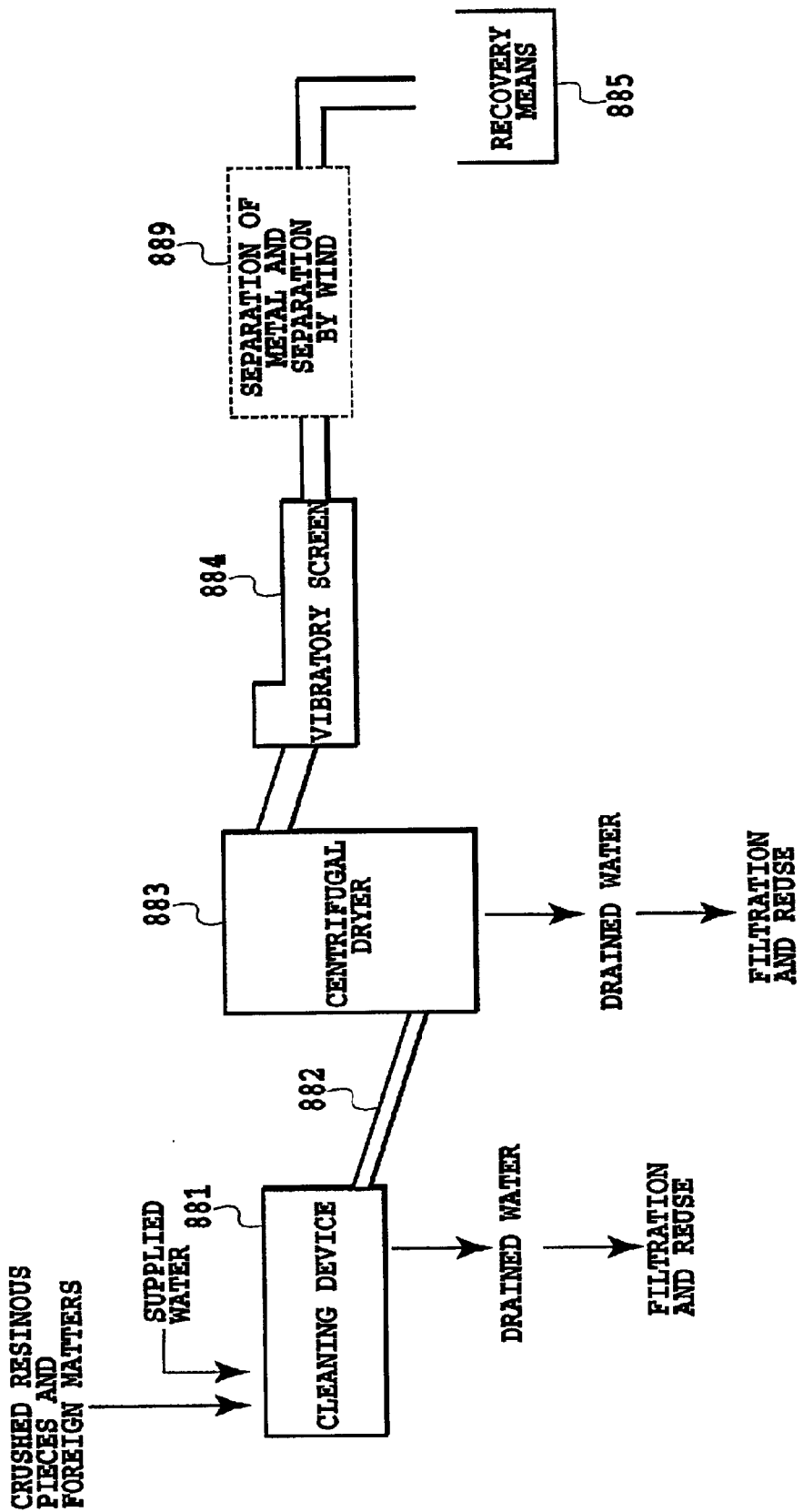
FIG. 16 is a block diagram illustrating one embodiment of recovery means according to the present invention.

A device illustrated in FIG. 16 separates the crushed resinous pieces from the foreign matters by rinsing the mixture thereof with water, discharges the foreign matters as thus separated together with water and recovers the remaining crushed resinous pieces.

On the surface of the crushed resinous piece cleaned by the cleaning system 600 as described above, foreign matters (dust derived from coated film, plated layer or label) scrubbed or scraped off from the crushed resinous pieces by the cleaning operation are adhered. This mixture (of the crushed resinous particles and the foreign matters) is initially introduced into a continuous type rinsing device 881 and rinsed with water. Most of the foreign matters adhered to the surface of the crushed resinous pieces are removed therefrom together with water in this process. This water may be reused after being filtrated.

The crushed resinous pieces thus rinsed are transferred via a pipe 882 to a centrifugal dryer 883 in which the dehydration is carried out. The crushed resinous pieces thus dehydrated are conveyed while vibrating on a vibratory screen 884, whereby the residual foreign matters are removed. Thereafter, the pieces are collected by a predetermined recovery means. In this regard, subsequent to the vibratory screen 884, means 889 may be provided for further removing metallic particles by using magnetic force or foreign matters by using wind.

Thus, the recycling of resin is carried out.

EXAMPLES

Results of the crushing operation carried out by using the above-mentioned embodiment of the crusher described above are shown in Table 1 of FIG. 17. The specifications of this crusher are as follows:

Size of entrance port: 300 mm×600 mm

Width of chain conveyor: 340 mm

Motor: 5.5 kW

Rotational speed of conveyor: 50 rpm

Number of crushing blades in connecting plate: 2 rows× 18/a plate

Opposite member: fixing plate with slits

I-[1] Example A

Twenty resinous parts were manually extracted from discarded copying machines. Although having various sizes and shapes, the parts were all mold products having a plate-thickness of approximately 2 to 3 mm. The maximum length thereof was 630 mm. These were classified into two groups in accordance with the criterion whether or not the product has a size in which two of a length, a width and a height are 280 mm×170 mm or less.

[1-1] Five parts had a size of 280 mm×170 mm or less, a total weight of which was 2.3 kg.

[1-2] Fifteen parts had a size exceeding 280 mm×170 mm, a total weight of which was 9 kg.

These mold products were crushed by the crusher shown in FIG. 3 (the specifications of which were as described above).

Results were shown in Table 1 of FIG. 17. In Table 1, an equivalent diameter of a projection circle in Table 1 is defined as a diameter of a circle having the same area as a projected area of a particle (see KAGAKU KOGAKU BINRAN, 5th edition, p.219). In this Example, an image of about 100 particles placed on a flat surface while taking care not to overlap with each other was shot, from which the number and the individual area are measured by an image-processing technique. Then a total of the areas was divided by the number of particles to obtain an average area, from which a diameter of a circle having the same area is calculated.

I-[2] Comparative Example A

A trial was made to treat the same resin mold products as used in Example A with a small size crusher UG-280 (effective aperture 280 mm×170 mm, 5.5 kW) manufactured by K.K. HORAI and added with a screen of 15 mm However, the resin mold products in the group [1-2] (exceeding 280 mm×170 mm) could not be introduced into the small size crusher UG-280 of K.K. HORAI and thus could not be crushed.

II-[1] Example B (Regarding the Identification)

The following three mold products 1. to 3. of different kinds of resins (a box having a size of 15 cm×10 cm×10 cm and a thickness of 3 mm) were individually crushed by the crusher UG-280 manufactured by K.K. HORAI (with a screen of 20 mm mesh). An average size of the crushed resinous piece was approximately 10 mm as represented by an equivalent diameter, wherein the equivalent diameter is a diameter of a circle having the same area as a projected area of the crushed resinous piece.

The above crushed resinous pieces are respectively packed in separate bags (made of polyethylene and having a size of 23 cm long, 17 cm wide and 40 μm thick). Kinds of the resins were identified by a resin identification device (RP-1, manufactured by Spectracode; based on the Raman spectrum analysis), upon which a time required for the identification was measured. Results are shown in Table 2 of FIG. 18. In Table 2, ○ represents cases wherein all the samples could be identified, and X represents cases wherein there are samples not identified.

1. Acrylonitrile-butadiene-styrene
2. Polystyrene
3. Polycarbonate/acrylonitrile-butadiene-styrene II-[2] Comparative Example B (Regarding the Identification)

Comparative example B was carried out in the same manner as in Example B, except that the above-mentioned three resin mold products 1. to 3. were crushed all together, not separately, in the crusher and the three kinds of resinous pieces were identified as they are by the resin identification device, respectively, without being packed in the bag. Results are shown in Table 2 of FIG. 18.

In Table 2, the number of test samples was assumed by the following equation:

Number of test samples=weight of resin mold product before crushing/standard weight of crushed piece The weight of the resin mold product before crushing was 702 g and the standard weight of the crushed piece was 0.259 g, whereby the number of the test samples was 2700. This value is about 900 times that in Example B. In this regard, an average weight of ten disk-like pieces having the equivalent diameter of approximately 10 mm was used as the standard weight of the crushed piece.

In Table 2, the time required for the identification was assumed by the following equation:

Time required for identification=all weights of crushed pieces/weight of crushed pieces which could be identified within one minute All the weights of the crushed pieces was 702 g and the weight of the crushed pieces which could be identified within one minute was 5.21 g, whereby the time required for the identification was 135 minutes. This value is about 900 times that in Example B. In this regard, in the crushed pieces having the equivalent diameter of 1 mm or less, there were those difficult to be positioned to the identification device or impossible to be identified because the intensity of Raman spectrum becomes weak.

Next, an example regarding the cleaning system will be described.

OA apparatuses collected from the market were disassembled to separate housings made of ABS resin which were then crushed by using a marketed crusher (UG-280; manufactured by K.K. HORAI, with a screen of 10 mm mesh) into crushed resinous pieces and subjected to a cleaning treatment. There were paper seals on part of the housing and many contaminants on the surface due to a long time use or the collection, disassembly or classification operation. Hereinafter, such crushed resinous pieces are referred to as crushed pieces (A).

In a similar manner, housings made of ABS resin and having a coating on the surface thereof were crushed into crushed pieces (B) which were then cleaned.

III-[1] Example C (Regarding the Cleaning by the Horizontal Type Continuous Cleaning Device Shown in FIGS. 12 and 13)

(1) Cleaning device used

A diameter of a screw blade provided on a rotary shaft of the cleaning device was 100 mm and a length of the device was 25 times the diameter of the screw blade; i.e., 2.5 m. A drainage port had slits of 1.2 mm wide. A water level was maintained somewhat higher than the rotary shaft by the water level adjustment pipe, so that a weight of crushed pieces (A) and that of rinsing water are generally equal to each other.

Further, the screw blades and cleaning plates constituted by semicircular disks arranged on the rotary shaft at a pitch of 40 mm with a phase thereof being shifted at 90 degrees to each other were alternately disposed on the rotary shaft so that a ratio of an axial length to the diameter thereof becomes 2 to 4. Part of the screw blade was cut off to adjust the conveying capacity. The inner surface of the vessel and the surfaces of the screw blades and the cleaning plates were roughened to have the irregularity of 50 to 100 μm deep.

(2) Cleaning operation

Crushed pieces (A) were introduced into the entrance port of this cleaning device at a rate of 50 kg/hr. On the other hand, water was fed from the entrance port at a rate of 30 kg/hr and also from two water ports provided in the lengthwise intermediate portion of the device. These water supply rates were regulated so that a drainage rate from an open end of the drainage line becomes 100 kg/hr.

The cleaning operation was carried out at a rotational speed of the rotary shaft of 400 rpm (corresponding to a linear speed of 2.1 m/sec at a tip end of the cleaning plate) to obtain a slurry in which dust such as the paper seals blocked to pass by the slits is mixed with the treated crushed pieces (A) from the exit port. The slurry was dispersed on the vibratory screen of 2 mm mesh while spraying water from above to separate and remove pieces of the paper seals or dust therefrom. Thereafter, the crushed pieces were dehydrated through a centrifugal dryer and dried. Then, through a wind classifier, foreign matters having a small specific weight which could not removed by the water spray were separated and removed to obtain completely cleaned crushed pieces.

(3) Inspection of foreign matters

Crushed pieces of 10 g were compression-mold between a pair of clean aluminum foils put in a gap between stainless steel plates at a temperature of 220° C. and a pressure of 4 MPa to result in a sheet of approximately 200 mm diameter. Thereafter, the aluminum foils were peeled off from this sheet, and opposite sides of the sheet were observed by a magnifying glass to count the number of foreign matters. Results are shown in Table 3 of FIG. 19.

III-[2] Comparative Example C

A trial was made to clean the crushed pieces (A) in the same manner as in Example C, except that water is not used. In a short time after beginning the introduction of crushed pieces, however, the crushed pieces began to melt, whereby a load became large to disable the operation.

III-[3] Comparative Example D

A rotational speed at which the crushed pieces are not melted was studied in Comparative example C, and it was found that such a speed is 50 rpm (corresponding to a linear speed of 0.26 m/sec at a tip end of the cleaning plate). The cleaning operation was carried out at this rotational speed in the same manner as in Comparative example C in which water is not used. After being cleaned, the crushed pieces (A) discharged from the exit port were post-treated in the same manner as in Example C to separate and remove the foreign matters. Foreign matters left in the crushed pieces were observed in the same manner as in Example C. Results are shown in Table 3 of FIG. 19.

III-[4] Example D

The crushed pieces (B) were cleaned in the same manner as in Example C except that a water supply rate from the intermediate portion increases so that a drainage rate is regulated to 200 kg/hr at the open end of the drainage line. After being cleaned, the crushed pieces (B) discharged from the exit port were post-treated in the same manner as in Example C to separate and remove foreign matters. Foreign matters left in the crushed pieces were observed in the same manner as in Example C. Results are shown in Table 3 of FIG. 19.

III-[5] Comparative Example E

The cleaning was carried out in the same manner as in Example D except that the rotational speed of the rotary shaft decreases to 50 rpm. After being cleaned, the crushed pieces (B) discharged from the exit port were post-treated in the same manner as in Example C to separate and remove foreign matters. Foreign matters left in the crushed pieces were observed in the same manner as in Example C. Results are shown in Table 3 of FIG. 19.

III-[6] Example E (Regarding the Cleaning by the Batch Type Cleaning Device of a Vertical Type Shown in FIG. 15)

This cleaning device had a vessel having an inner diameter of 400 mm and a height of 500 mm, in which lattice type blades having an outer diameter of 360 mm is provided at a center. The inner surface of the vessel and all surfaces of the lattice type blades were roughened to have the irregularity of 200 to 300 µm deep.

The crushed pieces (A) of 22 kg and water of 20 kg were introduced into this cleaning device, and a height of the water level adjustment pipe is regulated to the water level at this instant. The cleaning operation was carried out for 20 minutes by rotating the lattice type blade at 300 rpm and supplying and draining water at a rate of 20 l/hr. After being cleaned, the cleaned crushed pieces (A) were taken out therefrom by opening the piston-shaped discharge valve. The crushed pieces were post-treated in the same manner as in Example C to separate and remove foreign matters. Foreign matters left in the crushed pieces were observed in the same manner as in Example C. Results are shown in Table 3 of FIG. 19.

III-[7] Comparative Example F

The cleaning operation was carried out in the same manner as in Example E except that a crusher in which the inner surface of the vessel and surfaces of the agitator blades are not roughened. After being cleaned, the cleaned crushed pieces (A) were taken out therefrom by opening the piston-shaped discharge valve. The crushed pieces were post-treated in the same manner as in Example C to separate and remove foreign matters. Foreign matters left in the crushed pieces were observed in the same manner as in Example C. Results are shown in Table 3 of FIG. 19.

It is apparent from Table 3 of FIG. 19 that there are extremely less foreign matters in the crushed pieces after being cleaned by roughening part of the crusher to be in contact with the crushed pieces. Particularly there are none of foreign matters, of which the maximum length exceeds 0.25 mm. On the other hand, it is also apparent that; in Comparative example C, the operation of the crusher is impossible due to the melting of crushed pieces; in Comparative examples D and F, particularly in D, a number of foreign matters are left in the treated crushed pieces; and in Comparative example E, the number of foreign matters is uncountable because of a large amount of remnants derived from coated film. In other words, Comparative examples are all extremely inferior.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A resin recycling system comprising crushing means for individually crushing resin mold products into crushed resinous pieces in which 70% or more of the crushed resinous pieces have an equivalent diameter in a range from 1 to 50 mm;

packing means for separately packing the individually crushed resinous pieces the said packing means including a bag having a transparent portion;

classification means for irradiating a light beam to the individually crushed resinous pieces through the transparent portion of the bag and identifying a kind of the crushed resinous pieces based on a reflected beam therefrom, and clarifying the bags into respective kinds of resins; and cleaning means capable of taking the crushed resinous pieces out from the bag and cleaning the crushed resinous pieces to remove foreign matters adhered on the surface thereof said cleaning means comprising a cleaning vessel, an agitating member provided in the cleaning vessel, and an abrasive surface provided on at least part of the inner wall of the cleaning vessel and/or the surface of the agitating member.

2. A resin recycling system as defined as claim 1, further comprising recovery means for separating foreign matters from a mixture of the crushed resinous pieces and the foreign matters, and recovering the crushed resinous pieces.

3. A resin recycling system as defined by claim 1, further comprising:

conveyer means for conveying the bag and wherein said classification means comprises identification means, provided in the vicinity of a predetermined identification position on a conveying path of said conveyer means, for irradiating a light beam to the individually crushed and separately packed resinous pieces through the transparent portion of the bag passing by the identification position and identifying the kind of crushed resinous pieces based on a reflected beam therefrom, and storage means for storing the identified kind of crushed resinous pieces and being capable of estimating an expected arrival time at which the bag of the crushed resinous pieces would reach a predetermined classification position on the conveying path.

4. A resin recycling system comprising:

a crusher that includes an endless conveyor for conveying individual polymer mold products, and an opposed member having an opposed surface confronting at least one end of said endless conveyer on a conveying-directional side and disposed so that a distance between the opposed surface and a conveying surface of said endless conveyer becomes smaller in a conveying direction, wherein crushing edges or crushing pins are provided on at least one of the conveying surface of said endless conveyer and the opposed surface of said opposed member, and a gap between the conveyor and the opposed member is formed to crush the resinous pieces with said crushing edges or pins;

a packaging device including a bag having a transparent portion;

an identification device for irradiating a light beam to the crushed resinous pieces through the transparent portion of the bag and detecting the reflected beam or the dispersed beam from the crushed resinous pieces by a sensor element, and identifying a kind of the polymer product based on a detected result, wherein said sensor element is disposed at a predetermined position in the vicinity of a conveying path of the crushed resinous pieces; and a device for cleaning the crushed pieces that include a vessel and agitating blades, wherein the vessel has an entrance port for crushed resinous pieces and a water supply port, both provided in an upper portion thereof, and an exit port for the crushed resinous pieces and a drainage port, both provided in a lower portion provided thereof; and drainage line for adjusting a water level being connected to the drainage port, and at least part of the surface of the vessel and/or surfaces of the agitating blades being roughened to make them abrasive.

* * * * *